US012196741B2

(12) United States Patent
Clements et al.

(10) Patent No.: US 12,196,741 B2
(45) Date of Patent: Jan. 14, 2025

(54) DEVICES AND SYSTEMS WITH INTEGRATED ELECTRODES OR OPTICAL ELEMENTS FOR MONITORING CELL CULTURES AND RELATED METHODS

(71) Applicant: AXION BIOSYSTEMS, INC., Atlanta, GA (US)

(72) Inventors: Michael Antony Clements, Johns Creek, GA (US); Isaac Perry Clements, Marietta, GA (US); Thomas J. O'Brien, Atlanta, GA (US); James David Ross, Decatur, GA (US); Daniel Christopher Millard, Atlanta, GA (US); Andrew Willsie, Lilburn, GA (US); Edgar A. Brown, Decatur, GA (US); Robert Dixon Grier, Jr., Atlanta, GA (US); Amanda Jervis Preyer, Atlanta, GA (US); Denise Danielle Sullivan, Atlanta, GA (US)

(73) Assignee: AXION BIOSYSTEMS, INC., Atlanta, GA (US)

( * ) Notice: Subject to any disclaimer, the term of this patent is extended or adjusted under 35 U.S.C. 154(b) by 770 days.

(21) Appl. No.: 17/425,571

(22) PCT Filed: Jan. 27, 2020

(86) PCT No.: PCT/US2020/015206
§ 371 (c)(1),
(2) Date: Jul. 23, 2021

(87) PCT Pub. No.: WO2020/154727
PCT Pub. Date: Jul. 30, 2020

(65) Prior Publication Data
US 2022/0349869 A1 Nov. 3, 2022

Related U.S. Application Data

(60) Provisional application No. 62/870,123, filed on Jul. 3, 2019, provisional application No. 62/796,838, filed on Jan. 25, 2019.

(51) Int. Cl.
*G01N 33/483* (2006.01)
*G01N 21/59* (2006.01)
(Continued)

(52) U.S. Cl.
CPC ......... *G01N 33/4836* (2013.01); *G01N 21/59* (2013.01); *G01N 27/02* (2013.01); *G01N 33/48735* (2013.01)

(58) Field of Classification Search
CPC ......... G01N 33/4836; G01N 33/48728; G01N 33/48735; G01N 21/59; G01N 27/02
See application file for complete search history.

(56) References Cited

U.S. PATENT DOCUMENTS 4,250,266 A * 2/1981 Wade .................. C12M 27/10
435/286.2
4,974,594 A 12/1990 Berlin
(Continued)

FOREIGN PATENT DOCUMENTS

JP 2016-529889 A 9/2016
JP 2017-505139 A 2/2017
(Continued)

OTHER PUBLICATIONS

Logos biosystems article entitled "Monitoring confluency of adherent cells in multi-ell plates using the Celena® X High Content Imaging System", author unknown, publication date unkown. (Year: 2024).*
(Continued)

*Primary Examiner* — Alexander S Noguerola
(74) *Attorney, Agent, or Firm* — Meunier Carlin & Curfman LLC

(57) ABSTRACT

A scalable, real-time, label-free, electrode- or optical-based cell monitoring system for integration into a cell culture incubator is described herein. An example system includes
(Continued)

(1) cell culture consumables with integrated electrodes and/or optics for growing and monitoring cells, (2) incubator trays for consumable organization and recording, and (3) a system console, external to the incubator, for connecting multiple incubator trays. Without perturbing the cell culture, the system is capable of monitoring multiple culture attributes for each cell culture consumable simultaneously. These attributes can include, but are not limited to, cell growth, proliferation, morphology, media pH, or media oxygen. The system can support multiple trays, which permits monitoring dozens to hundreds of consumables simultaneously, including a mixture of consumables of various sizes. In addition to monitoring adherent cells, the disclosed technology can be readily adapted for monitoring of cell suspensions.

16 Claims, 16 Drawing Sheets

(51) Int. Cl.
*G01N 27/02* (2006.01)
*G01N 33/487* (2006.01)

(56) References Cited

U.S. PATENT DOCUMENTS

| | | | |
|---|---|---|---|
| 5,563,067 A | 10/1996 | Sugihara et al. | |
| 5,672,505 A * | 9/1997 | Jones | C12M 25/02 422/561 |
| 6,403,333 B1 * | 6/2002 | Anglade | C12Q 1/04 422/50 |
| 6,873,719 B1 * | 3/2005 | Holley | C12M 41/46 382/141 |
| 7,148,059 B1 | 12/2006 | Tillotson et al. | |
| 9,329,168 B2 | 5/2016 | Rajaraman et al. | |
| 10,067,117 B2 | 9/2018 | Tyler et al. | |
| 2004/0058453 A1 * | 3/2004 | Free | G01N 33/442 422/50 |
| 2005/0237065 A1 | 10/2005 | Kudoh et al. | |
| 2007/0215269 A1 * | 9/2007 | Weil | B65B 7/164 156/308.2 |
| 2009/0197243 A1 * | 8/2009 | Rieder | C12Q 1/02 435/5 |
| 2010/0190228 A1 | 7/2010 | Giaever et al. | |
| 2011/0117542 A1 | 5/2011 | Abassi et al. | |
| 2011/0275538 A1 | 11/2011 | Sonkusale | |
| 2013/0038727 A1 | 2/2013 | Clark | |
| 2013/0139618 A1 | 6/2013 | Chaussin et al. | |
| 2014/0162348 A1 * | 6/2014 | Katsumoto | G01N 33/86 435/287.1 |
| 2014/0274796 A1 | 9/2014 | Hickman | |
| 2016/0215248 A1 | 7/2016 | Keitel et al. | |
| 2017/0015964 A1 | 1/2017 | Agabi | |

FOREIGN PATENT DOCUMENTS

| | | |
|---|---|---|
| WO | 2007001248 A1 | 1/2007 |
| WO | 2015012955 A1 | 1/2015 |
| WO | 2015192089 A1 | 12/2015 |
| WO | 2017125499 A1 | 7/2017 |

OTHER PUBLICATIONS

Extended European Search Report for Application No. 20744987.7 dated Oct. 20, 2022.
Communication Pursuant to Rule 164(1) EPC dated Aug. 17, 2022.
Jochen Scholz et al.: "Standardized online biomass measurement In single-use fermentation".
"BioPAT Viamass—Standardized Online Biomass Measurement in Single-Use Fermentation", Product Information Datasheet.
Clements Isaac P et al.: "Optogenetic stimulation of multiwell MEA plates for neural and cardiac applications", Progress in Biomedical Optics and Imaging, vol. 9690, Mar. 8, 2016 (Mar. 8, 2016).
Office Action issued in corresponding JP App. No. 2021-542400 mailed Jan. 5, 2024 (with English-language translation), 7 pages.
International Search Report and Written Opinion issued in PCT/US2020/015206, dated Apr. 23, 2020, 13 pages.

* cited by examiner

DEVICES AND SYSTEMS WITH INTEGRATED ELECTRODES OR OPTICAL ELEMENTS FOR MONITORING CELL CULTURES AND RELATED METHODS

CROSS-REFERENCE TO RELATED APPLICATIONS

This application claims the benefit of U.S. provisional patent application No. 62/796,838, filed on Jan. 25, 2019, and entitled "DEVICES AND SYSTEMS WITH INTEGRATED ELECTRODES FOR MONITORING CELL CULTURES AND RELATED METHODS" and U.S. provisional patent application No. 62/870,123, filed on Jul. 3, 2019, and entitled "DEVICES AND SYSTEMS WITH INTEGRATED ELECTRODES OR OPTICAL ELEMENTS FOR MONITORING CELL CULTURES AND RELATED METHODS," the disclosures of which are expressly incorporated herein by reference in their entireties.

BACKGROUND

Cell manufacturing is nuanced and can be very specific to the starting material and end goal. For example, stem cell manufacturing can include the process of differentiating stem cells into other cell types (e.g. neurons or cardiomyocytes). Such processes can be used to make small test samples or large manufacturing scale batches for commercial purposes. A drawback to existing methodologies is that highly trained and experienced experts must be closely involved in the process, often needing to make intuitive decisions based on visual assessments during critical steps. This approach is not readily transferable from operator to operator. A more practical manufacturing implementation would involve automatable processes that can be overseen by trained technicians without extensive specialized knowledge or experience.

Culture-based manufacture of cells (e.g. for therapeutic or investigative purposes), is currently regarded as an "art form" requiring expert operators to manage many dynamically changing variables simultaneously. Despite the use of strict protocols, the operator must still make nuanced real-time decisions (e.g. harvest times or media change frequency). These decisions are often driven by subjective "look and feel" assessments, whereby the operator notes changes in media color, cell appearance, or cell culture confluency. As a result, tracking important information about cells (e.g. in flasks or well plates) is tedious and error-prone. In person monitoring is done infrequently, providing a single snapshot of culture growth, instead of a continuous record. Observing cell growth over time provides important information about the culture and optimal times to perform culture steps like media changes and passaging. Moreover, with traditional methods, tracking key variables often involves perturbing the cells in a way that consumes cells and/or introduces risk to the health of the cells. Therefore, a solution is desired that not only non-invasively tracks key measures of cell behavior, but also easily scales to dozens or hundreds of flasks and plates.

In addition to difficulties monitoring key variables of cultured cells, the handling of cell cultures is cumbersome. A strict sterile environment must be maintained, and the quantities and concentrations of supporting media or investigative compounds must be precisely managed. These complications are further exacerbated when managing dozens to hundreds of culture flasks or plates. As a result, it is important for a scalable monitoring system to not only quantify and track key cell growth variables but also simplify cell monitoring and handling.

Basic attempts have been made in academic settings to use computer-assisted imaging techniques (e.g. bright field segmentation) to automate the scoring of cell images to predict the quality of the cells and when to add reagents to trigger the next phase of the differentiation process. These techniques continue to rely on technicians to remove and image the plates. Other confluence monitoring systems are used in conjunction with extremely large culture and automation equipment. These types of systems are unobtainable for all but large scale manufacturers. Both of these types of systems only capture a snapshot of culture growth, when the plate is removed from the incubator and imaged, instead of a comprehensive system for monitoring cell culture growth and maintenance. Other alternatives provide very detailed images of cultures, which could be used to identify confluence, but are more suited to fundamental research. This type of solution is not scalable to the many plates or flasks that are often used in research and manufacturing.

Cell manufacturing differs in key aspects from traditional, non-biological manufacturing techniques. Due to variability in the culture starting material, the cell manufacturing process needs to be flexible to produce a consistent end-product. For example, a given batch of cells may require an additional day in culture to mature before harvesting. Consequently, a live label-free read-out of batch performance would allow cell manufacturing to be optimized on a batch by batch basis.

Cell manufacturing can also be very expensive. For example, a single manufacturing batch can cost ten thousand to thirty thousand dollars. A significant proportion of this cost (e.g. 50%) can be attributed to labor. Reducing "contact-time" with the product would dramatically reduce labor costs.

Furthermore, it is often not until the end of the manufacturing process (after >20 days or more) that cell batch success or failure is known using traditional techniques. Abandoning a failing batch (or flask) as soon as possible (i.e. "failing fast and failing cheap") would reduce manufacturing costs.

Current testing techniques are often not predictive and furthermore require consumption of cells. For example, flow cytometry is often used, but cell structural markers are poor predictors of cell function and this test consumes a flask of cells at each sample point in the process. Both visualization and electrophysiology are commonly used to monitor the stages of stem cell development, but these require additional culture handling.

Researchers can now make cell models that replicate human diseases etc. using stem cell technologies. Unfortunately, there is often considerable variability in the iPSC or embryonic stem cell (ESC) starting material which makes the cell differentiation process unreliable (wasting both time and money). Additionally, some biological materials are still used in the differentiation process which introduces a further source of variability. Consequently, making stem cell-derived cell models is more similar to growing tomatoes than manufacturing plastic "widgets".

Previously, in vitro electrophysiology read-out tools, such as the MAESTRO MEA system from AXION BIOSYSTEMS, INC. of Atlanta, Georgia, have been used in various stages of cell production. For example, in process development stages within a research and development setting, electrophysiology assessment tools are used to inform the adjustment of manufacturing techniques to obtain cells with desired electrophysiological properties. Electrophysiology tools can similarly be used to perform quality control assessment of manufactured cell batches. While electrophysiology systems have been used to inform the design of the manufacturing process and for product release criteria, there has been little development towards making electrophysiology assessment techniques part of in-process control—providing a real-time read-out of cell batch performance, without the need for perturbing or consuming the cells.

Imaging is also a commonly used tool in cell culture and development. Culture batches are often observed to determine their health and confluence to establish where in the process a culture is at the time of imaging. Imaging measurements are used to determine the timing of media changes and culture passaging. When this process is performed by hand, results are skewed by the technician performing the assessment and measurements are performed infrequently. Currently, when the process is automated, the assessment is performed a single plate at a time, in series. The frequency of these measurements do not provide a detailed picture of how the culture is progressing over time.

A scalable system that continuously measures of cell culture and culture media conditions, without perturbing or consuming cells, would optimize the cell culture process.

SUMMARY

The systems, devices, and methods described herein monitor cell culture confluence and media conditions, as well as record key culture information, for example hours in culture, passage number, and cell line; providing comprehensive information about the culture process and the individual cultures. This provides users (e.g., manufacturers and researchers) with a fuller picture of growth as the cells progress towards confluence. Moreover, the scale of the systems and devices described herein is unique. These systems provide continuous monitoring for dozens to hundreds of cultures, as opposed to existing low volume devices.

A scalable, real-time, label-free, electrode and/or optics-based cell monitoring system for integration into a cell culture incubator is described herein. An example system includes (1) standard cell culture consumables and/or cell culture consumables that include integrated electrodes, sensors, or optics for growing and monitoring cells, (2) incubator trays or drawers for consumable organization, imaging, and electrical recording, and (3) a system console, external to the incubator, for connecting multiple incubator trays. Without perturbing the cell culture, the system is capable of monitoring multiple culture attributes for each cell culture consumable simultaneously. Alternatively, the culture attributes can be monitored serially, but sufficiently fast enough as to be nearly continuous, on the scale of culture growth. Measurement attributes can include, but are not limited to, cell growth, proliferation, morphology, confluence, cell-cell junction strength, adhesion strength, media pH, or media oxygen. Additionally, fluorescent and/or optogenetic labels and other optical techniques for tagging and imaging can be used to monitor protein expression, spatial localization of proteins, or other intracellular properties or characteristics. The system can support multiple trays, which permits monitoring dozens to hundreds of consumables simultaneously, including a mixture of culture plates, flasks, bottles, or other cell culture containers of various sizes. In addition to monitoring adherent cells, the system can be adapted for monitoring of cell suspensions.

An example cell culture consumable is described herein. The cell culture consumable can include a container, and a plurality of electrodes integrated into the container, where the electrodes are distributed across an internal surface of the container.

In some implementations, the electrodes are embedded in the internal surface of the container.

In some implementations, the electrodes are disposed on the internal surface of the container.

Alternatively or additionally, the cell culture consumable further includes an electrical connector arranged on an external surface of the container, and a plurality of routing traces electrically connecting the electrodes and the electrical connector.

Alternatively or additionally, the container defines an opening, and the cell culture consumable further includes a lid for sealing the opening. The lid maintains a sterile environment within the container.

Alternatively or additionally, the electrodes include single electrodes, pairs of electrodes, bipolar electrodes, tripolar electrodes, or tetrapolar electrodes.

Alternatively or additionally, the electrodes include electrodes having different sizes and/or shapes.

Alternatively or additionally, the electrodes are arranged as an electrode array.

Alternatively or additionally, the electrodes are configured for at least one of impedance sensing, voltage sensing, neurotransmitter sensing, pH sensing, oxygen sensing, glucose sensing, or chemical sensing. Optionally, the electrodes include a first set of electrodes configured for impedance sensing or voltage sensing and a second set of electrodes configured for at least one of neurotransmitter sensing, pH sensing, oxygen sensing, glucose sensing, or chemical sensing.

Alternatively or additionally, the container is a flask, a bottle, a cell culture bag, a Petri dish, or a bioreactor.

Alternatively or additionally, the cell culture consumable further includes a machine-readable tag.

In some implementations, an example cell culture consumable can be a standard flask or plate that includes built-in optical features, including light guides, lenses, or texturing to aid in imaging. For example, an example cell culture consumable can include a container, and an optical element integrated into the container. The consumable can also optionally include a fluorophore or other sensor for culture media evaluation.

In some implementations, the optical element is a lens, a microlens, a filter, a prism, a mirror, a light guide, or a textured surface.

Alternatively or additionally, the cell culture consumable includes a sensor configured for at least one of neurotransmitter sensing, pH sensing, oxygen sensing, glucose sensing, or chemical sensing.

Alternatively or additionally, the cell culture consumable includes a machine-readable tag.

Alternatively or additionally, the container defines an opening, and the cell culture consumable further includes a lid for sealing the opening. The lid maintains a sterile environment within the container.

Alternatively or additionally, the container is a flask, a bottle, a cell culture bag, a Petri dish, or a bioreactor.

An example system is also described herein. The system can include a plurality of cell culture consumables and a tray including a plurality of slots configured to receive the cell culture consumables. Each of the cell culture consumables can include a container and a plurality of electrodes, where the electrodes are integrated into the container.

In some implementations, the slots include slots having different sizes and/or shapes.

Alternatively or additionally, each of the cell culture consumables and each of the slots includes a respective electrical connector. The respective electrical connectors for a corresponding cell culture consumable and slot are configured to be removably coupled to each other. Additionally, the respective electrical connectors for the corresponding cell culture consumable and slot are configured to communicate a signal collected by the electrodes of the cell culture consumable to the tray.

Alternatively or additionally, the tray includes a display device configured to visually display respective statuses of the cell culture consumables.

Alternatively or additionally, the system includes an incubator configured to receive the tray.

Alternatively or additionally, the system includes a plurality of trays, where each tray includes a plurality of slots configured to receive the cell culture consumables.

Alternatively or additionally, the system includes an electronic unit including a processor and a memory. The electronic unit is operably coupled to the tray through a communication link, for example. Alternatively, the electronic unit is incorporated into the tray. The electronic unit is configured to record a respective signal collected by the electrodes of each of the cell culture consumables.

In some implementations, the electrodes of each of the cell culture consumables are configured for at least one of impedance sensing, voltage sensing, pH sensing, oxygen sensing, glucose sensing, or chemical sensing, and the electronic unit is configured to measure at least one of impedance, voltage, pH, oxygen concentration, glucose concentration, or chemical concentration for each of the cell culture consumables. Optionally, the electronic unit is further configured to monitor at least one of cell growth, cell proliferation, cell morphology, or a cell culture medium for each of the cell culture consumables. Optionally, the electronic unit is further configured to provide in-process control feedback for each of the cell culture consumables such as a visual display, an audible alarm, an email, a text message, or combinations thereof.

In some implementations, the electronic unit is further configured to measure impedance for at least one of the cell culture consumables. Optionally, the electrodes of the at least one of the cell culture consumables are arranged as an electrode array, and the electronic unit is configured to generate a two-dimensional impedance map across the electrode array. Optionally, the electronic unit is further configured to create a real-time growth curve using the impedance for the at least one of the cell culture consumables. Optionally, the electronic unit is further configured to estimate cell culture confluency using the real-time growth curve for the at least one of the cell culture consumables. Optionally, the electronic unit is further configured to analyze the real-time growth curve and provide in-process control feedback for the at least one of the cell culture consumables.

In some implementations, the electronic unit is further configured to measure voltage and detect electric field potential for at least one of the cell culture consumables. Optionally, the electrodes of the at least one of the cell culture consumables are arranged as an electrode array, and the electronic unit is further configured to generate a two-dimensional electric field potential map across the electrode array. Optionally, the electronic unit is further configured to analyze the electric field potential and provide in-process control feedback for the at least one of the cell culture consumables.

In some implementations, the electronic unit is further configured to measure at least one of pH or oxygen concentration for at least one of the cell culture consumables.

In some implementations, the electronic unit is further configured to analyze the pH or oxygen concentration and provide in-process control feedback for the at least one of the cell culture consumables.

In some implementations, the electronic unit is further configured to deliver electrical stimulation via the electrodes of at least one of the cell culture consumables.

In some implementations, the system further includes a robot with a robotic arm configured to receive the tray or the cell culture consumable. The electronic unit can be operably coupled to the robot such that the electronic unit is further configured to control the robotic arm to pick up and move the tray or the cell culture consumable from a first position to a second position.

In some implementations, the system further includes an optical module including at least one of a light source or an optical detector.

In some implementations, each of the cell culture consumables comprises a respective machine-readable tag, and the system further includes a scanner configured to read the respective machine-readable tags.

In some implementations, an example system can include a plurality of cell culture consumables and a tray including a plurality of slots configured to receive the cell culture consumables. Each of the cell culture consumables can include a container, where each container includes built-in light guide or optics, or a standard container that contains built-in sensors for culture environment monitoring.

In some implementations, an example system can include a plurality of cell culture consumables and a tray including a plurality of slots configured to receive the cell culture consumables. Each of the cell culture consumables can include a container. The system can also include an optical system comprising a light source and a detector. The optical system can be configured to continuously monitor at least one of cell growth, cell proliferation, or cell morphology over time based on an amount of light detected by the detector after reflection, refraction, or transmission by a cell culture.

In some implementations, the optical system is configured to simultaneously monitor at least one of cell growth, cell proliferation, cell morphology, or fluorescent or optogenetic labels in each of the cell culture consumables.

In some implementations, the slots include slots having different sizes and/or shapes.

In some implementations, the optical system includes an array of light sources. Alternatively or additionally, the optical system includes an array of detectors.

In some implementations, the system includes a respective optical element corresponding to each of the cell culture consumables. Optionally, the respective optical elements are integrated into the respective containers of the respective cell culture consumables. For example, the respective optical element integrated into the container is a lens, a microlens, a filter, a prism, a mirror, a light guide, or a textured surface.

Alternatively or additionally, each of the cell culture consumables includes a respective machine-readable tag, and the system further includes a scanner configured to read the respective machine-readable tags.

In some implementations, the optical system is further configured to monitor a cell culture medium.

Alternatively or additionally, the system further includes an incubator configured to receive the tray.

Optionally, the system includes a plurality of trays, where each tray includes a plurality of slots configured to receive the cell culture consumables.

Alternatively or additionally, the system includes an electronic unit including a processor and a memory. The electronic unit is operably coupled to the tray through a communication link, for example. Alternatively, the electronic unit is incorporated into the tray. The electronic unit is configured to record the amount of light detected by the detector after reflection, refraction, or transmission by the cell culture.

In some implementations, the system further includes a sensor configured for at least one of neurotransmitter sensing, pH sensing, oxygen sensing, glucose sensing, or chemical sensing, and the electronic unit is further configured to receive a signal from the sensor.

In some implementations, the electronic unit is further configured to provide in-process control feedback based on the signal received from the sensor such as a visual display, an audible alarm, an email, a text message, or combinations thereof.

In some implementations, the electronic unit is further configured to measure at least one of cell confluence, cell-cell junction strength, or adhesion strength of the cell culture. Optionally, the electronic unit is further configured to generate a two-dimensional map of the cell confluence across the at least one of the cell culture consumables. Optionally, the electronic unit is further configured to create a real-time growth curve using the cell confluence for the at least one of the cell culture consumables. Optionally, the electronic unit is further configured to analyze the real-time growth curve and provide in-process control feedback for the at least one of the cell culture consumables. Optionally, the at least one of cell confluence, cell-cell junction strength, or adhesion strength of the cell culture is measured using a light-field imaging technique. Alternatively or additionally, the at least one of cell confluence, cell-cell junction strength, or adhesion strength of the cell culture is measured using a digital inline holographic microscopy (DIHM) technique.

In some implementations, the system further includes a robot with a robotic arm configured to receive the tray or the cell culture consumable. The electronic unit can be operably coupled to the robot such that the electronic unit is further configured to control the robotic arm to pick up and move the tray or the cell culture consumable from a first position to a second position.

Another example cell culture consumable is described herein. The cell culture consumable includes a container, an electrode integrated into the container, and an optical element integrated into the container. Optionally, the cell culture consumable further includes a plurality of electrodes integrated into the container, where the electrodes are distributed across an internal surface of the container.

An example method is also described herein. The method can include recording a signal from a cell culture consumable. Each of the cell culture consumables can include a container and a plurality of electrodes, where the electrodes are integrated into the container. The signal is detected by the electrodes. The method can also include using the signal to measure a parameter of the cell culture consumable, and monitoring at least one of cell growth, cell proliferation, cell morphology, or a cell culture medium for the cell culture consumable based on the parameter.

In some implementations, the parameter is at least one of impedance, voltage, pH, oxygen concentration, glucose concentration, or chemical concentration.

Additionally, the method optionally further includes providing in-process control feedback for the cell culture consumable such as a visual display, an audible alarm, an email, a text message, or combinations thereof.

Another example method is described herein. The method can include optically imaging cells from a standard culture consumable or one with built-in optical enhancements. Imaging can be done using traditional optical techniques or can be done as an indirect measure of light refraction, reflection, or transmission. Each of the cell culture consumables can optionally include a sensor which could be a fluorophore or electrical sensor to detect culture conditions, which may include pH, $CO_2$, or $O_2$, or environmental conditions can be monitored through optical imaging of particles in the media or media color in the presence of an indicator.

Another example method is described herein. The method can include illuminating a cell culture in at least one of a plurality of cell culture consumables, each cell culture consumable including a container, detecting an amount of light reflected, refracted, or transmitted by the cell culture, and continuously monitoring at least one of cell growth, cell proliferation, cell morphology, fluorescent or optogenetic labels of the cell culture over time.

Optionally, the method further includes measuring at least one of cell confluence, cell-cell junction strength, or adhesion strength of the cell culture.

Alternatively or additionally, the method optionally further includes measuring pH, oxygen concentration, glucose concentration, or chemical concentration within the at least one of the cell culture consumables.

Alternatively or additionally, the method optionally further includes optically monitoring a cell culture medium.

Alternatively or additionally, the method optionally further includes providing in-process control feedback for the at least one of the cell culture consumables such as a visual display, an audible alarm, an email, a text message, or combinations thereof.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 10A illustrates a method for manufacturing a cell culture consumable where holes are drilled in the consumable. FIG. 10B illustrates a method for manufacturing a cell culture consumable where discrete conductive members or an array of conductive members are inserted into holes drilled in the consumable. FIG. 10C illustrates a method for manufacturing a cell culture consumable where discrete conductive members attached to conductive traces (e.g., wires) are provided inside the consumable.

FIG. 19A is a perspective view of the system. FIG. 19B is another perspective view of the system.

DETAILED DESCRIPTION

Figure 1:
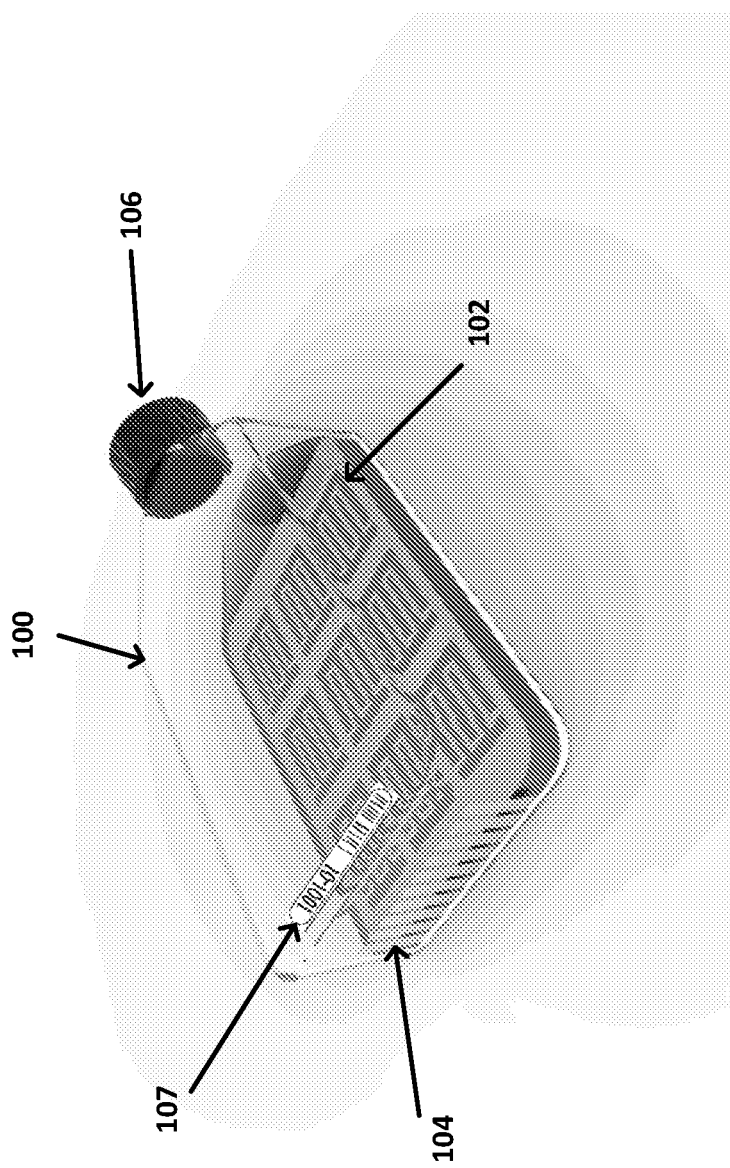
FIG. 1 is an illustration of an example cell culture consumable according to implementations described herein.
Figure 2:
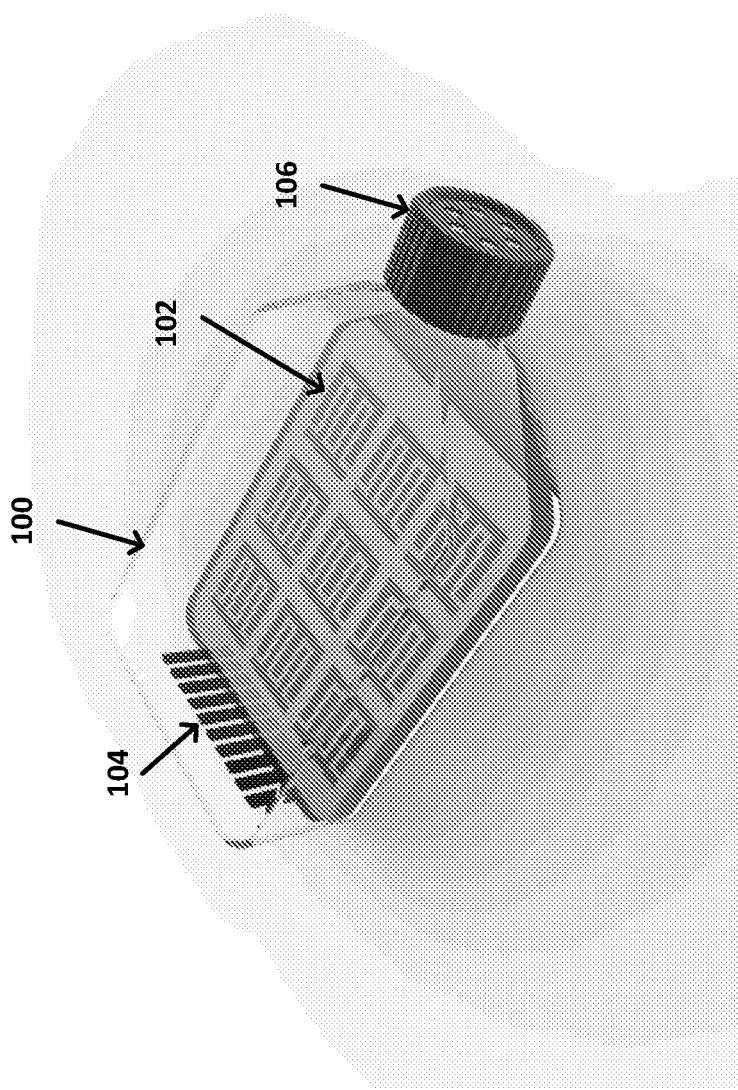
FIG. 2 is another illustration of an example cell culture consumable according to implementations described herein.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Devices and systems with integrated electrodes for monitoring cell cultures are described herein. Additionally, in-process methods for monitoring cell cultures are described herein. An electrode-based monitoring technology can satisfy the need for a multi-parameter cell monitoring system that is both scalable and easy to use. Embedding electrodes into the surfaces of cell culture vessels (also referred to herein as "cell culture consumables") allows for continuous, real-time tracking of key measures in a cost-effective manner. Moreover, operators can track a plurality of culture vessels (e.g., dozens to hundreds of culture vessels) without touching or perturbing the vessels.

Additionally, devices and systems to optically monitor cell growth and culture health through direct or indirect methods are also described herein. Optical imaging of cells at low or no magnification using one or more optical detectors can be used to monitor cell growth in a scalable manner. While the detector can include optics, additional advantage can be obtained by including an optical element such as light guides, texturing, or lenses, built directly into the consumable. Additionally, computational image processing methods can be used with the devices and systems described herein to improve monitoring of cell growth and culture health. Light sources and detectors can be stationary, placed in an array, or moveable. At low magnification and high scan rates, or by using multiple detectors, culture monitoring can be performed at sufficient rates to effectively monitor many culture consumables at a time.

In some implementations, the electrode-based system described herein is comprised of three components: 1) cell culture consumables with integrated electrodes for growing and monitoring cells, (2) trays for consumable organization and recording, and (3) a system console, external to the incubator, for communicatively connecting multiple trays. Optionally, the cell culture consumables of the electrode-based system can further include an optical element and/or a sensor, which can be used to monitor the growing cells. Optionally, in some implementations, the optical element and/or sensor is integrated into the cell culture consumable.

In some implementations, the optical-based system described herein can include three components: 1) cell culture consumables with or without integrated optical elements for growing and monitoring cells, (2) trays for consumable organization and recording, and (3) a system console, external to the incubator, for communicatively connecting multiple trays. Optionally, the cell culture consumables of the optical-based system can further include an electrode and/or a sensor, which can be used to monitor the growing cells. Optionally, in some implementations, the electrode and/or sensor is integrated into the cell culture consumable.

Electrodes and/or sensors embedded in the cell culture flask (also referred to herein as "cell culture consumable") or optical detectors give a live readout of cell culture status (e.g. cell number, variability/patchiness of cell culture, or metabolic status of the cell environment). Using predefined acceptance criteria, either pre-programmed by the system, or based on criteria established by the operator for the specific cell preparation, the system can notify the operator (e.g. via screen display, email, or text message) of how the cell culture is performing relative to these acceptance criteria. For example, the operator can be notified if cells are growing/dividing more slowly than normal, which can indicate that the culture is suboptimal for differentiation or will not perform well in a downstream assay. The operator can be notified as to when cell cultures are ready to be "split" or passaged, so that cell proliferation is not reduced due to contact inhibition. Notifications to the operator can also signal that the cell culture medium should be replaced (e.g., before the end of a work week, so the medium does not need to be changed over the weekend). As another example, notifications can indicate that the cell culture is not growing consistently across the flask and so should be discarded.

Advantages of the systems and devices described herein include, but are not limited to, reducing contact-time required by human operators, reducing the required expertise of human operators, and/or reducing the number of failed manufacturing batches.

Referring now to FIGS. 1-8, an example cell culture consumable and example electrode-based system are described. This disclosure contemplates that the example cell culture consumable and system can be used to monitor adherent cells or to monitor cell suspensions. As used herein, a "consumable" is intended to be consumed, e.g., the consumable is used and then replaced. The cell culture consumable can include a container 100, and a plurality of electrodes 102 integrated into the container 100, where the electrodes 102 are distributed across an internal surface of the container 100. As used herein, the "internal surface" of the container 100 is exposed to the cells and/or culture medium, while the "external surface" of the container 100 is opposite to the "internal surface", i.e., the "external surface" of the container 100 is exposed to the environment/user/operator. Accordingly, one or more electrodes 102 are integrated into an interior surface of the cell culture consumable, and electrode-based measures—such as impedance, pH, oxygen, voltage, and others—can be collected from the cell culture non-invasively in real time (e.g., in-process monitoring). This facilitates the ability to provide the user with a continuous, real-time readout of the electrode-based measures over time. This disclosure contemplates that the cell culture can include, but is not limited to, stem cells, immortalized cell lines, induced pluripotent stem cells (iPSCs), embryonic stem cells (ESCs), or autologous or allogeneous cells for transplant. Optionally, by arranging electrodes 102 (e.g., impedance-sensing electrodes) into an array adds a spatial dimension, which can be used to monitor adherent cell confluency across large area. In some implementations, the electrodes 102 are embedded in the internal surface of the container 100. For example, the electrodes 102 can be embedded in consumable materials on the surfaces of the container 100 that are exposed to cells or cell media. In other implementations, the electrodes 102 are disposed on the internal surface of the container 100. This disclosure contemplates that the electrodes 102 are part of the container 100, which is in contrast to merely placing an electrode inside of the container 100. For example, the electrodes 102 can be integrated into the container 100 during the manufacturing process.

Additionally, the cell culture consumable can further include an electrical connector 104 arranged on the external surface of the container 100, and a plurality of routing traces electrically connecting the electrodes 102 and the electrical connector 104. The routing traces can be integrated into the container 100, for example, during the manufacturing process. For example, the routing traces can be embedded in the container 100 and/or disposed on a surface of the container 100. Similarly to the electrodes 102, the routing traces are part of the container 100, which is in contrast to merely placing a conductor (e.g., wire) inside of the container 100. Accordingly, signals collected by electrodes 102 provided in the interior of the cell culture consumable can be routed to the externally-facing electrical connector 104 (e.g., contact pads), which allows for a transmission of internally-collected signals to external hardware (e.g., a tray 200 and/or an electronic unit 300) for quantification and/or analysis. As described herein, this disclosure contemplates that the cell culture consumables can optionally include one or more optical elements and/or environmental sensors in addition to the integrated electrodes.

The electrodes 102 can include single electrodes, pairs of electrodes, bipolar electrodes, tripolar electrodes, tetrapolar electrodes, or combinations thereof. In some implementations, two or more of the electrodes 102 have the same size and/or shape, while in other implementations two or more of the electrodes 102 have different sizes and/or shapes. It should be understood that the container 100 can include two or more electrodes 102 having the same size and/or shape and two or more electrodes 102 having different sizes and/or shapes. Optionally, in some implementations, the electrodes 102 can be arranged as an electrode array, which adds a spatial dimension to the collected signals. Configuring electrodes 102 into an array affords several advantages, including redundancy and spatial resolution (e.g. 2D mapping of cell activity across regions of a culture or from across the entire culture). Electrode array-based platforms also provide capabilities for automation: collecting similar data with multiple electrodes, providing redundancy, improving measurement accuracy, and/or allowing for automated algorithms to identify key regions of interest. Alternatively or additionally, the electrodes 102 can be configured for at least one of impedance sensing, voltage sensing, neurotransmitter sensing, pH sensing, oxygen sensing, glucose sensing, or chemical sensing. Optionally, the electrodes 102 can include a first set of electrodes configured for impedance sensing or voltage sensing and a second set of electrodes configured for at least one of neurotransmitter sensing, pH sensing, oxygen sensing, glucose sensing, or chemical sensing. As used herein, a "set of electrodes" can include one or more electrodes. It should be understood that two sets (i.e., first and second sets) of electrodes are provided only as an example. This disclosure contemplates providing a container having more than two sets of electrodes (e.g., three, four, five, etc.), where different sets of electrodes are configured for different sensing types.

As described herein, voltage can be recorded from the electrodes 102 and processed to detect signals of interest. For example, stem cell differentiation from induced pluripotent stem cells (iPSCs) into cardiomyocytes will result in the production of electrical field potentials signals as the cardiomyocytes develop and mature. Spikes in the voltage signal (which is recorded by the electrodes 102), indicating field potential depolarizations of the cells, can be detected by analyzing the voltage signals with an electronic unit (described below).

Alternatively or additionally, impedance can be measured from one or more of the electrodes 102. Impedance of the one or more electrodes is calculated from the current and voltage through an electrode. As cells attach to the surface of the container 100 and increasingly cover the electrode(s), the impedance of the electrode(s) increases. Changes in the electrode impedance can be used to estimate cell culture confluence for adherent cells, or cell number for nonadherent cells. For various cell types, there is an optimal time to "split" or "passage" the cells into new containers (e.g. flasks), and this time point can be evaluated based on the confluency of the cells. Based on the known dimensions of the impedance sensing electrode(s), the electronic unit can be configured to estimate the percent confluency of the cell culture coverage in a continuous manner, which can then be used to determine optimal time to "split" the cells. The user can then be alerted to the optimal time to "split" the cells based on a threshold for cell confluency. Optionally, the threshold is pre-set, user-controlled.

Alternatively or additionally, oxygen concentration, pH, glucose concentration, or other chemical sensing (e.g. sensing of neurotransmitters like dopamine and 5HT (serotonin) using fast scan cyclic voltammetry electrodes) can be measured from one or more of the electrodes 102. In some implementations, the electrodes 102 can be coated with materials that transduce chemical analytes into electrically measurable signals or otherwise improve the sensitivity to pH, oxygen, chemical sensing, or impedance. The media used to propagate induced pluripotent stem cells or define a differentiation pathway can contain expensive small molecules and thus be wasteful to change media too soon, but also can lead to cell damage or death if not changed. Thus, the electrodes 102 can be used to measure conditions of the cell culture media. For example, a critical component of the media is the pH, and the pH sensing signal can be analyzed dynamically to determine the optimal time to change the media for cell health purposes.

Further, the container 100 can define an opening, and the cell culture consumable can include a lid 106 for sealing the opening. It should be understood that the lid helps maintain a sterile environment within the container 100. The container 100 shown in the figures is a flask. It should be understood that a flask is only one example type of container 100. This disclosure contemplates that the container 100 can be a bottle, a cell culture bag, a Petri dish, a bioreactor, or other type of consumable for culturing cells.

Optionally, the container 100 can include a machine-readable tag 107. The machine-readable tag 107 can be a computer-readable label such as a one-dimensional (1D) or two-dimensional (2D) bar code. Alternatively, the machine-readable tag 107 can be a radiofrequency identification (RFID) tag. It should be understood that bar codes and RFID tags are provided only as example machine-readable tags. This disclosure contemplates that the machine-readable tag 107 can be any type of identifier provided on the container (e.g., printed on, embedded in, disposed on, attached to, etc.) that are capable of being read by a machine.

An example system can include a plurality of cell culture consumables and a tray 200 (also referred to herein as "drawer"). Cell culture consumables are described above. For example, each of the cell culture consumables can include a container 100 and a plurality of electrodes 102, where the electrodes 102 are integrated into the container 100 as described above. The system can optionally include a light source and optical detector integrated into the tray. As described herein, optical imaging can be used to assess the culture growth. Additionally, each of the cell culture consumables can optionally include one or more optical elements and/or environmental sensors as described herein. The tray 200 can include a plurality of slots 202 configured to receive the cell culture consumables. In some implementations, two or more of the slots 202 have the same size and/or shape (e.g., to accommodate the same type of consumables), while in other implementations two or more of the slots 202 have different sizes and/or shapes (e.g., to accommodate different types of consumables). It should be understood that the tray 200 can include two or more slots 200 having the same size and/or shape and two or more slots 200 having different sizes and/or shapes. The tray 200 can therefore be configured to support multiple consumable types, including various sizes of flasks (e.g., T75, flasks, T25 flasks, T225 flasks), bottles, Petri dishes, cell culture bags, and/or other cell culture vessels. Despite changes in conformation of the cell culture consumable, all tray configurations can include slots 202. These slots can be configured with electrical connectors 204 (e.g., connector pins or springs) to make connections to the electrical connectors 104 of the cell culture consumables. Optionally, the electrical connector 104 for each of the cell culture consumable can be designed to allow for rapid, simple attachment to a corresponding electrical connector 204 of a slot 202. Slot 202 can optionally include such features as keyed recesses with sloped surfaces that allow cell culture consumables to naturally "settle" into the slots 202 in the proper orientation for culture vessel docking. The system can optionally include a scanner (e.g., bar code scanner) for reading machine-readable tags, which facilitates culture vessel identification and experiment management.

As discussed above, each of the cell culture consumables can include an electrical connector 104. Additionally, each of the slots 202 can include an electrical connector 204. In other words, each of the cell culture consumables and each of the slots can include a respective electrical connector 104 and 204, respectively. Accordingly, the respective electrical connectors 104 and 204 for a corresponding cell culture consumable and slot can be removably coupled to each other. In this way, the respective electrical connectors 104 and 204 for a corresponding cell culture consumable and slot can communicate a signal (or signals) collected by the electrodes 102 (e.g., collected inside the cell culture consumable) to the tray 200. The electrode-integrated cell culture consumables can be operably connected to hardware (e.g., tray 200) that captures signals routed from the internal, cell-facing electrodes to the electrical connector 104 (e.g., contact pads) arranged externally. These signals can then be passed to an electronic unit (described below) for further analysis, processing, and/or quantification.

Optionally, the system can include an incubator 400. For example, the consumable-interfacing tray 200 can reside (1) within the incubator 400 for cell environmental control, (2) support rapid and simple device connection and alignment to minimize challenges in multi-consumable handling, (3) occupy a small space to permit multiple trays or drawers in the incubator 400 and/or (4) contain a scanner or other means to identify a consumable for experiment management information. Additionally, the tray 200 can provide visual feedback (e.g., via display device 206) to rapidly communicate the statuses of the cell culture consumables to a user/operator. Optionally, the communication link 305 (e.g., cable) that supports power and data functions is small, so as to fit through small incubator ports. Electronics within the trays 200 can be designed to withstand the warmer, high-humidity environments of the incubator 400. It is contemplated that wireless connections can be used in various implementations. The tray size can be selected to allow the trays to rest on one or more incubator shelves. Optionally, a dense stacking mechanism can be used to pack many trays 200 into a small vertical area of the incubator 400. The shelves of the incubator 400 can be designed with a mechanism to allow each tray 200 to be pulled out, like a dresser drawer, without tipping the plane of the tray 200. Optionally, the incubator 400 can also be configured to house multiwell plates in addition to trays 200.

The system can optionally further include an electronic unit 300 (sometimes referred to as a "console"). The electronic unit 300 can include a processor and a memory. For example, the electronic unit 300 can be a computing device such as computing device 900 of FIG. 9. In some implementations, the electronic unit 300 can be incorporated into a tray 200. In some implementations, the electronic unit 300 can be incorporated into the incubator 400, which is configured to receive the tray 200 or a plurality of trays 200 as described above. In some implementations, the electronic unit 300 can be separate from the tray 200 and/or the incubator 400. The electronic unit 300 can be operably coupled to the tray 200 and/or the incubator 400 using a communication link 305. This disclosure contemplates the communication link 305 is any suitable communication link. For example, a communication link may be implemented by any medium that facilitates data exchange between the electronic unit 300 and the tray 200 and/or the incubator 400 including, but not limited to, wired, wireless and optical links. Example communication links include, but are not limited to, a local area network (LAN), a wireless local area network (WLAN), a wide area network (WAN), a metropolitan area network (MAN), USB, Ethernet, the Internet, or any other wired or wireless link such as WiFi, WiMax, 3G or 4G.

In some implementations, the trays 200, which hold the cell culture consumables, can be disposed inside the incubator 400 as described above. Additionally, as described herein, trays 200 can be configured to work with automation systems to receive a consumable from a robot or automated incubator. Additionally, the trays 200 can connect to the electronic unit 300, which can optionally be located outside of the incubator 400. The electronic unit 300 can accept signals from multiple trays simultaneously, and is optionally configured to identify tray and consumable types automatically. The electronic unit 300 can include a computing system, a display, and custom electronics to manage computations for data to and from the trays 200. Optionally, the display can be a touch-sensitive display. The electronic unit 300 can execute software that reports on all sensors and sensing modalities. Work flows and process boundaries can be defined to automatically alert operators to actions (e.g. "change media") or problems (e.g. "growth rate out of spec"). The software can be designed to make dozens to hundreds of simultaneously growing cultures easy to track and handle.

The electronic unit 300 can be configured to record a respective signal collected by the electrodes 102 of each of the cell culture consumables. This information can be stored in memory of the electronic unit 300. As described above, each cell culture consumable can include a plurality of electrodes 102. Accordingly, it should be understood that the electronic unit 300 can record a plurality of signals from the same cell culture consumable in some implementations. Additionally, the electronic unit 300 can record a plurality of signals from each of a plurality of cell culture consumables. As described herein, the electrodes 102 of each of the cell culture consumables can be configured for at least one of impedance sensing, voltage sensing, pH sensing, oxygen sensing, glucose sensing, or chemical sensing and the electronic unit 300 can be configured to measure at least one of impedance, voltage, pH, oxygen concentration, glucose concentration, or chemical concentration for each of the cell culture consumables. The signals collected by the electrodes 102 and recorded by the electronic unit 300 can be used to monitor the cell culture, for example, to provide real-time, continuous monitoring and/or in-process controls. Additionally, the electronic unit 300 can be configured to monitor at least one of culture history, cell growth, cell proliferation, cell morphology, or a cell culture medium for each of the cell culture consumables. This disclosure contemplates the such information can be monitored using the signals collected by the electrodes 102. For example, in one implementation, the electrodes 102 can be used to measure voltage signals, from which field potential depolarizations of cardiomyocytes, which differentiated from iPSCs, can be detected. Optionally, the cell culture consumable can further include a fluorophore sensor in addition to the electrodes 102, and the electronic unit 300 can be further configured to monitor environmental conditions inside the cell culture consumable and/or cell culture medium itself, for example, using the measurements detected by the fluorophore sensor. Optionally, the electronic unit 300 can be configured to provide in-process control feedback for each of the cell culture consumables. The in-process control feedback can be, but is not limited to, a visual display, an audible alarm, an email, a text message, or combinations thereof. In-process control feedback can be provided in response to the signals collected by the electrodes 102 and optionally analyzed by the electronic unit 300. Optionally, the in-process control feedback can be displayed at a display device 310 of the electronic unit 300.

In some implementations, the electronic unit 300 can be configured to measure impedance for at least one of the cell culture consumables. The signals collected by the electrodes 102 and recorded by the electronic unit 300 can be used to measure impedance. Impedance calculation can be performed either by injecting a current and measuring the voltage corresponding voltage, or applying a voltage and measuring the corresponding current. Impedance can be used to estimate cell culture confluency. Optionally, impedance can be separated into real and imaginary parts and used to differentiate between cell coverage, confluency, cell-to-cell connectivity, and barrier function. Optionally, as described herein, the electrodes 102 of the at least one of the cell culture consumables are arranged as an electrode array, and the electronic unit 300 can be configured to generate a two-dimensional impedance map across the electrode array. This provides direct information about cell culture uniformity and growth conditions across the consumable. Optionally, the electronic unit 300 can be configured to create a real-time growth curve using the impedance for the at least one of the cell culture consumables. Additionally, the electronic unit 300 can be configured to estimate cell culture confluency using the real-time growth curve for the at least one of the cell culture consumables. The electronic unit 300 can be further configured to analyze the real-time growth curve and provide in-process control feedback for the at least one of the cell culture consumables. Analysis can be based on historical data from previous batches of similar cells, current batches of the same cells, user defined criteria, or preset settings. The in-process control feedback can be, but is not limited to, a visual display, an audible alarm, an email, a text message, or combinations thereof. Optionally, the in-process control feedback can be displayed at a display device 310 of the electronic unit 300.

In some implementations, the electronic unit 300 can be configured to measure voltage and detect electric field potential for at least one of the cell culture consumables. The signals collected by the electrodes 102 and recorded by the electronic unit 300 can be used to measure voltage and detect electric field potential. Optionally, as described herein, the electrodes 102 of the at least one of the cell culture consumables are arranged as an electrode array, and the electronic unit 300 can be configured to generate a two-dimensional electric field potential map across the electrode array. Field potential activity can be used as an indicator of culture stage of growth, culture health, culture maturity, and culture connectivity. It can also be used to track signal propagation through the culture in the case of closely coupled cells, for example cardiomyocytes. The electronic unit 300 can be configured to analyze the electric field potential and provide in-process control feedback for the at least one of the cell culture consumables. The in-process control feedback can be, but is not limited to, a visual display, an audible alarm, an email, a text message, or combinations thereof. Optionally, the in-process control feedback can be displayed at a display device 310 of the electronic unit 300.

In some implementations, the electronic unit 300 can be configured to measure at least one of pH or oxygen concentration for at least one of the cell culture consumables. The signals collected by the electrodes 102 and recorded by the electronic unit 300 can be used to measure pH or oxygen concentration of the culture medium. pH and/or oxygen concentration can be used as indicators for changing the culture medium. The electronic unit 300 can be configured to analyze the pH or oxygen concentration and provide in-process control feedback for the at least one of the cell culture consumables. pH detection can be done through photometric or potentiometric methods, using optical detection, fluorophores, or metal electrodes. The in-process control feedback can be, but is not limited to, a visual display, an audible alarm, an email, a text message, or combinations thereof. Optionally, the in-process control feedback can be displayed at a display device 310 of the electronic unit 300.

Optionally, in some implementations, the system can include a built-in stimulator configured to generate electrical stimulation. For example, electrical stimulation can be used to control or pattern activity in developing cells. Also, electrical stimulation can speed up the maturation of hiPSC cells (e.g. cardiomyocytes or neurons.) Stimulation can be used to induce electroporation with strong stimulation, to aid in the delivery of compounds. Stimulation can also be used for long- or short-term stimulation to provide pacing, induce maturity, create electric fields, or to elicit electrotaxis. This disclosure contemplates that the stimulator and electronic unit 300 can be operably coupled by a communication link, e.g., any link that facilitates data exchange between the electronic unit and stimulator. The stimulator can be a voltage source or a current source. This disclosure contemplates that the stimulator and the electrodes 102 can be coupled using a wired or wireless (e.g., radiofrequency (RF)) link. In some implementations, the stimulator can be operably coupled with the electrodes 102, for example, using electrical routing via the electrical connector 104. The stimulator can be configured to provide stimulus signals to the electrodes 102. The electronic unit 300 can be configured to control the stimulator to deliver electrical stimulation via the electrodes 102 of at least one of the cell culture consumables.

Optionally, in some implementations, the system can include a robot having a robotic arm. For example, the NIMBUS platform from HAMILTON COMPANY of Reno, Nevada is an example robotic systems used for automating cell culture processes. This disclosure contemplates that the system can also be interfaced to an automated transfer station of a cell culture incubator, for example the STX series automated incubators from Liconic Instruments of Mauren, Liechtenstein. Automated incubators and cell culture systems and robots are known in the art and are not described in further detail below. Optionally, the robot is operably coupled to the electronic unit 300. This disclosure contemplates that the robot and electronic unit 300 can be operably coupled by a communication link, e.g., any link that facilitates data exchange between the electronic unit and robot. The electronic unit 300 can be further configured to control the robotic arm to pick up and move a tray or a cell culture consumable from a first position to a second position. This is shown, for example, in FIGS. 19A and 19B, where a robot 1900 having a robotic arm 1950 is moving in proximity to a container 100. The robot 1900 can be used to transfer the container 100 to/from a tray 200. Alternatively or additionally, the robot 1900 can be used to transfer a tray 200 to/from the incubator 400. The tray 200 and/or container 100 can be moved using the robot 1900 for the purposes of measurement and/or imaging, for example.

It should be appreciated that the logical operations described herein with respect to the various figures may be implemented (1) as a sequence of computer implemented acts or program modules (i.e., software) running on a computing device (e.g., the computing device described in FIG. 9), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 9:
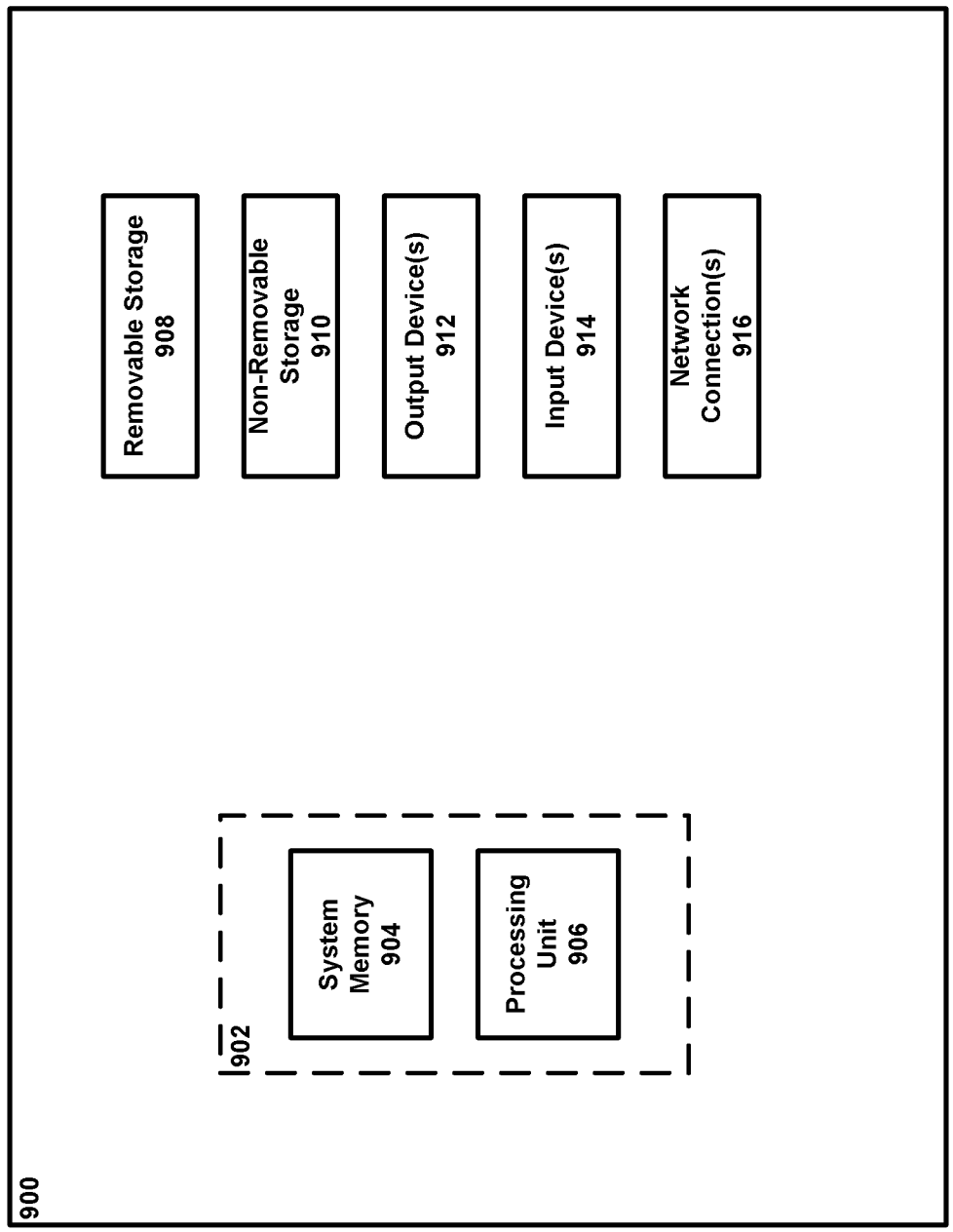
FIG. 9 is a diagram of an example computing device.

Referring to FIG. 9, an example computing device 900 upon which the methods described herein may be implemented is illustrated. It should be understood that the example computing device 900 is only one example of a suitable computing environment upon which the methods described herein may be implemented. Optionally, the computing device 900 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 900 typically includes at least one processing unit 906 and system memory 904. Depending on the exact configuration and type of computing device, system memory 904 may be volatile (such as random access memory (RAM)), non-volatile (such as read-only memory (ROM), flash memory, etc.), or some combination of the two. This most basic configuration is illustrated in FIG. 9 by dashed line 902. The processing unit 906 may be a standard programmable processor that performs arithmetic and logic operations necessary for operation of the computing device 900. The computing device 900 may also include a bus or other communication mechanism for communicating information among various components of the computing device 900.

Computing device 900 may have additional features/functionality. For example, computing device 900 may include additional storage such as removable storage 908 and non-removable storage 910 including, but not limited to, magnetic or optical disks or tapes. Computing device 900 may also contain network connection(s) 916 that allow the device to communicate with other devices. Computing device 900 may also have input device(s) 914 such as a keyboard, mouse, touch screen, etc. Output device(s) 912 such as a display, speakers, printer, etc. may also be included. The additional devices may be connected to the bus in order to facilitate communication of data among the components of the computing device 900. All these devices are well known in the art and need not be discussed at length here.

The processing unit 906 may be configured to execute program code encoded in tangible, computer-readable media. Tangible, computer-readable media refers to any media that is capable of providing data that causes the computing device 900 (i.e., a machine) to operate in a particular fashion. Various computer-readable media may be utilized to provide instructions to the processing unit 906 for execution. Example tangible, computer-readable media may include, but is not limited to, volatile media, non-volatile media, removable media and non-removable media implemented in any method or technology for storage of information such as computer readable instructions, data structures, program modules or other data. System memory 904, removable storage 908, and non-removable storage 910 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 906 may execute program code stored in the system memory 904. For example, the bus may carry data to the system memory 904, from which the processing unit 906 receives and executes instructions. The data received by the system memory 904 may optionally be stored on the removable storage 908 or the non-removable storage 910 before or after execution by the processing unit 906.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

An example method is also described herein. The method can include recording a signal from a cell culture consumable. Cell culture consumables are described above with regard to FIGS. 1-8. For example, each of the cell culture consumables can include a container (e.g., container 100) and a plurality of electrodes (e.g., electrodes 102), where the electrodes are integrated into the container. The signal is detected by the electrodes, which are located inside the container, and routed to electrical connectors arranged on the exterior of the container. The method can also include using the signal to measure a parameter of the cell culture consumable, and monitoring at least one of cell growth, cell proliferation, cell morphology, or a cell culture medium for the cell culture consumable based on the parameter. This disclosure contemplates that the systems and methods described herein can be used to provide in-process control of a cell culture as described below. Additionally, this disclosure contemplates that one or more signals can be recorded from each of a plurality of cell culture consumables. Optionally, such signals can be collected from a plurality of cell culture consumables simultaneously.

Example manufacturing methods for producing cell culture consumables (e.g., flasks or other cell culture vessels) are also described herein. In one implementations, the manufacturing method produces different components (e.g., pieces) of the consumable, which are then molded and/or bonded together to form the consumable. For example, it is possible to produce upper and lower portions and then mold the upper portion of the container and the bottom portion of the container separately, and then bond these two molded pieces together. Bonding methods can include, but are not limited to, ultrasonic welding, high temperature techniques, and adhesive bonding.

An optical-based consumable such as a flask lends itself strongly to molding. For example, lenses, microlenses and light guides can be designed directly into the upper, bottom, and/or side surfaces of the container. These surfaces can then be molded and bonded together. Prior to bonding, it is possible to add a sensor to the interior of the flask, as described below. This technique provides a cost effective and manufacturable consumable.

Several methods can be used for integrating electrodes and electric routing (e.g. circuit traces, vias, connectors) into a consumable. In one implementation, the bottom surface of a two-part consumable is "replaced" by a substrate (preferably transparent) with integrated electrodes and electronics. In this case, metal can be deposited directly on the surface of this substrate using a standard method. Standard methods include sputtering, evaporation, etc. Lift-off techniques can be used to define the pattern of the metal or a mask and control where the metal is placed. Conductive biocompatible inks can be printed on the substrate, using screen/stencil printing or inkjet technology. Screen printing, especially on a roll-to-roll system can be very cost efficient and scalable. Adhesives, or ultrasonic/thermal welding are examples of ways to attach the electrically functionalized bottom to the upper portion of the consumable.

In other implementations, the consumable can be manufactured using conventional techniques, and one or more openings or "windows" on the bottom piece of the consumable can be molded in or otherwise created, to allow substrates with integrated electrodes to be built into the consumable, thus circumventing the need for electrical routing elements or wire traces between the electrode and contact pad. In essence, the internal/cell-culture facing electrode and the external/electronics-facing contact pad share a common physical structure. These "circuits" or substrates with integrated electrodes and electronics, can be attached to the one or more openings on the consumable's bottom piece, for example with adhesives or welding. This method permits the insertion of electrodes onto any consumable surface, including the side-walls, which may provide an optimal surface for monitoring media attributes rather than cell confluency.

In other implementations, circuits can be made similarly to the substrates that attach to a multiwell plate such as multiwell plates described in U.S. Pat. No. 9,329,168 to Rajaraman et al., issued May 3, 2016, titled "DEVICES, SYSTEMS AND METHODS FOR HIGH-THROUGHPUT ELECTROPHYSIOLOGY," or U.S. Pat. No. 10,067,117 to Tyler et al., issued Sep. 4, 2018, titled "CELL-BASED BIOSENSOR ARRAY AND ASSOCIATED METHODS FOR MANUFACTURING THE SAME." For example, a thin film of transparent PET or similar plastic can have metal tracks electroplated to form a pattern on them (additive processing). The circuit can also be made from plastic films with metal coatings. The metal coatings are etched to reveal the pattern of interest (subtractive processing), similarly to standard PCB processes. Multiple windows can be distributed through the consumable to allow sensing from distributed regions across the culture or to provide multiple regions of different sensing modalities.

Figure 10A:
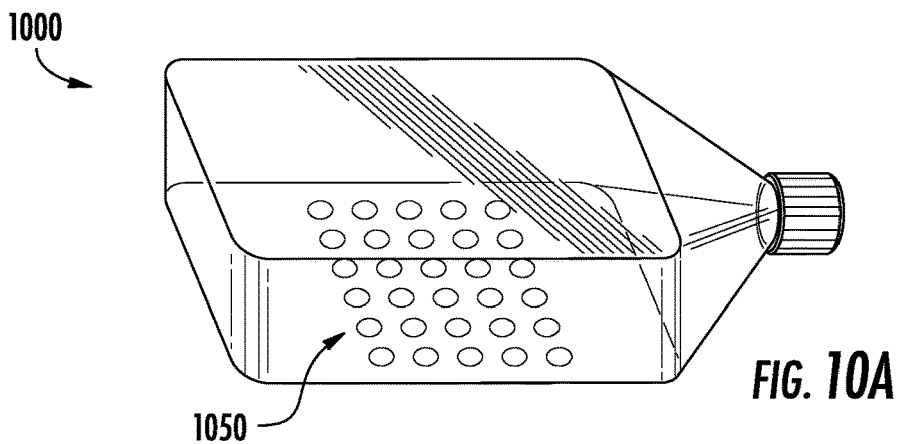
FIGS. 10A-10C are illustrations of example methods for manufacturing a cell culture consumable according to implementations described herein.
Figure 10B:
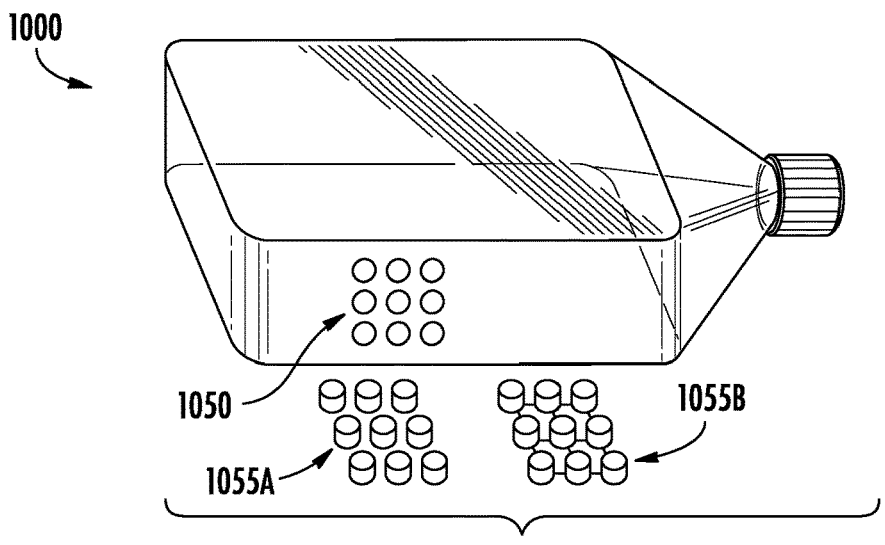
Figure 10C:
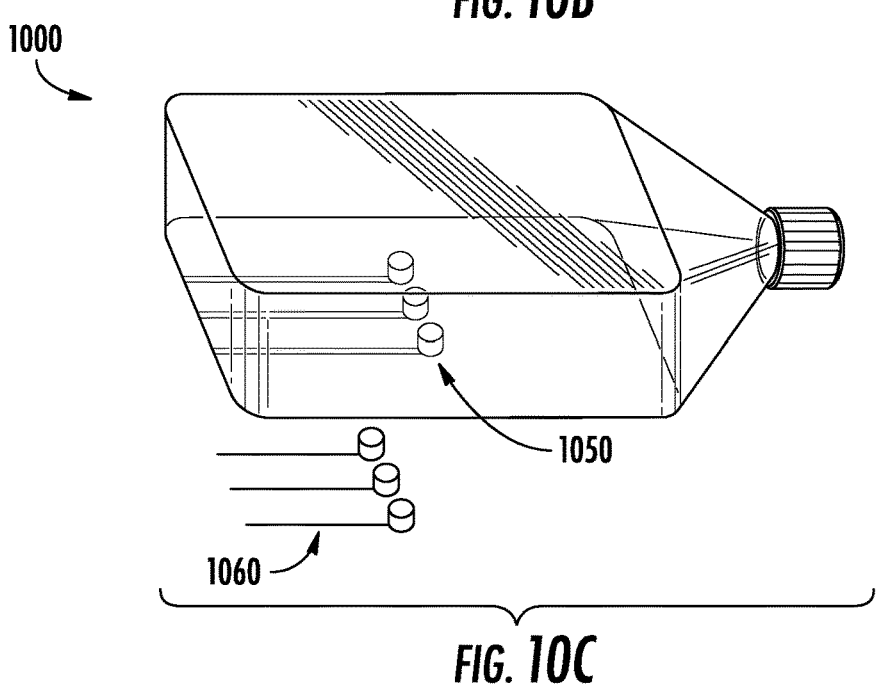

In another implementation, the circuit can be an insert into the consumable. This manufacturing method is illustrated by FIGS. 10A-10C. For example, in FIG. 10A, one or more holes 1050 (or, slots, or other openings) are formed (e.g., drilled) in a bottom portion of a consumable 1000. Such holes 1050 allow media/cell access to circuit/sensors. Although the holes 1050 are provided in the bottom portion of the consumable 1000 in FIG. 10A, it should be understood that holes can be provided in other portions or surfaces (e.g., top, bottom, sides, front, back, and/or lid) of the consumable 1000. Additionally, it should be understood that the number and/or arrangement of holes 1050 in FIG. 10A are provided only as an example. This disclosure contemplates manufacturing consumables with different numbers and/or arrangements of holes. Circuits/sensors can be affixed to the outside of the consumable 1000. While this arrangement can be used with transparent sensors, it can also be used for opaque embodiments. As shown in FIG. 10B, a plurality of holes 1050 are made in the consumable 1000. The holes 1050 are then fitted with a sensor. The sensor can be a plurality of discrete conductive members 1055A or an array of conductive members 1055B. It should be understood that the sensor is inserted from the exterior of the consumable 1000 through the holes 1050 provided therein. Also, this architecture can allow for some modularity in manufacturing if there are more sensor types than a single consumable could reasonably accommodate. The modularity can allow custom configurations of sensors. The holes, slots, or openings can be made on the top, bottom, sides, front, back, or lid of the consumable. For example, a slot can be incorporated into the bottom edge of the back or side of the consumable, such that a planar circuit can be slotted into the consumable to form all or part of the bottom of the consumable and then the slot sealed. Alternatively or additionally, as shown in FIG. 10C, the sensor can be discrete conductive members with conductors 1060 (e.g., wires) attached thereto. This disclosure contemplates that such sensor can be provided inside the consumable 1000.

In another implementation, the consumable can be solid plastic or other conventional material, optionally with a thinned bottom or regions of thinness on the bottom. Underlying electrode pads can be on the bottom exterior of this bottom, for example underlying thinned regions. The electrodes can capacitively couple to the cells or medium in the consumable to measure and/or stimulate. This method can reduce manufacturing cost of the consumable cell culture vessel and prevent the need to introduce different materials into the interior of the consumable and in contact with cells or culture medium. Optical stimulation or recording can also be performed in this manner. Thinning of the flask can enhance parameters of optical stimulation and measurement, including imaging.

Electrical vias are useful for routing electrical connections between layers in a substrate or from one side of the substrate to another. For implementations where a circuit is made inside the consumable, small holes can be made in the bottom surface of the consumable and filled with conductive inks, polymers, epoxies, or otherwise conductive materials. The ink can form a small pad on the bottom, or sides of the consumable, which allow electrical connection to a monitoring system. In some implementations, the conductive material forms the electrode and the via. For example, a round via of 100 micron diameter, when filled with conductive ink can directly form a 100 micron diameter electrode contact inside the consumable.

In some implementations, when the top of the flask is attached to the planar bottom (with embedded circuitry), the circuit can be made to overhang the planar bottom or the planar bottom can extend beyond the plane of the top piece. Either design allows the circuit to protrude out from the consumable once assembled. In the case of a flexible circuit, the circuit can then be bent around any of the edges of the consumable for electrical connection on the sides. For example a flexible circuit containing electrodes and connections can be bonded to a top piece and an overhanging edge of the flexible circuit designed to bend 90° to wrap around and affix to the side of the top portion of the consumable. For mechanical strength, the flexible circuit in this case can have a stiffener or other more rigid substrate on the portion that bonds to the top consumable piece. The flexible portion in this case can fold or wrap around to the bottom side of the rigid substrate in this design.

In some implementations, the circuit is inside the consumable, without electrical vias to the exterior. Instead the consumable lid or cap can make electrical connection with the circuit inside the consumable. The manner of connection can be akin to a lightbulb and socket. Screwing on the cap makes one or more electrical connections with the interior circuit in this case.

In other implementations, sensors can be more discrete, and formed from stock material, either through stamping, chemical etching, micromachining, cutting or some other standard method. Made of bulk material, such as a micromachined piece of metal electroplated with gold, individual electrode sensors could be bent 90° and pushed through the consumable material coming out the bottom, sides or top. This can be accomplished by heating one or both pieces to allow pre-formed plastic, designed to receive metal pieces, to melt and allow the electrode to be pushed through to the interior where it can make sensing connections.

Similarly to the technique above, sensors can be formed from bulk or stock material and placed into an injection molding system in a process similar to "overmolding" techniques. Plastic can be injected into the mold to form the bottom of the consumable. Sensors can be planar or have bends to span the injection molded plastic and allow metal pieces to have a contact pad outside the consumable once assembled. Planar sensors can be routed to an edge and out. The bonding of the top and bottom pieces would allow some metal to protrude which can be used for electrical connections.

Similar to above, sensors can be formed from bulk or stock material. The sensor can be placed on a consumable bottom that has holes in it. Part of the sensor is bent and fed through the hole. An epoxy is used to seal the hole. Similarly, electrodes can be designed to "snap" into the hole, or screw into a threaded hole, or be formed to self-tap threads into a normal hole.

All of the above techniques can apply to discrete application of sensors (e.g. separate pieces of metal are inserted into the flask) or an arrayed or more complex sensor arrangement. For example, a consumable can be manufactured with an array of pin holes on the bottom. A matching array of protruding electrodes can be designed to insert into the matching holes and sealed into place.

In some implementations, a side wall of the consumable can be formed from a standard PCB, with a piece that protrudes along the bottom of the consumable.

In some implementations specialized for cell manufacturing, there are multiple layers of substrates, stacked with spacing, to increase the achievable adherent surface array. This disclosure contemplates that one or more of these layers can be replaced all or in part by a functionalized circuit substrate. For example, one or more slots on the back or side of the consumable can allow the functionalized substrate layer or layers to be slotted in and then sealed in place for sterility and to prevent leakage.

It is understood that the above principles for integrating electrical or other types of sensors, transducers, actuators, etc. can be applied not just to rigid flasks, but to cell culture bags, bioreactors, stir-tank bioreactors, or any container/vessel for cell manufacturing.

Figure 16:
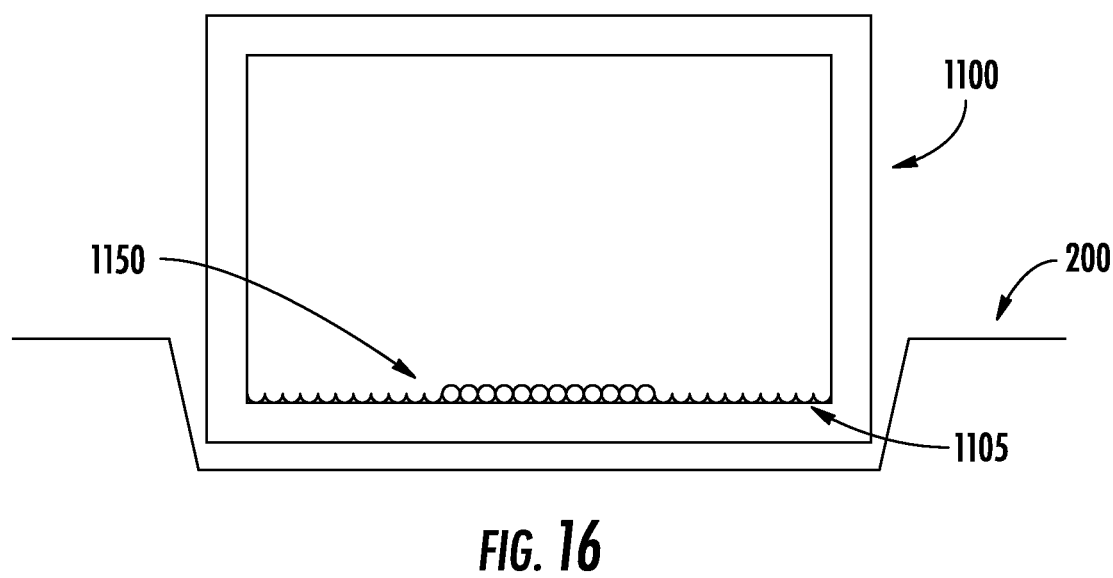
FIG. 16 is another illustration of an example cell culture consumable according to implementations described herein.
Figure 17:
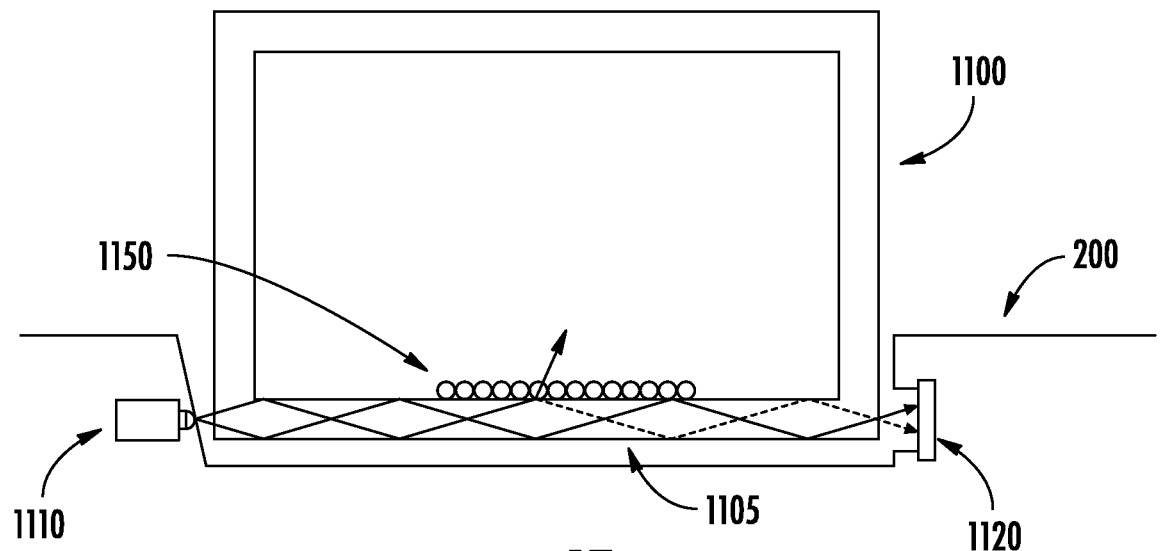
FIG. 17 is an illustration of a drawer for receiving cell culture consumables according to implementations described herein.
Figure 18:
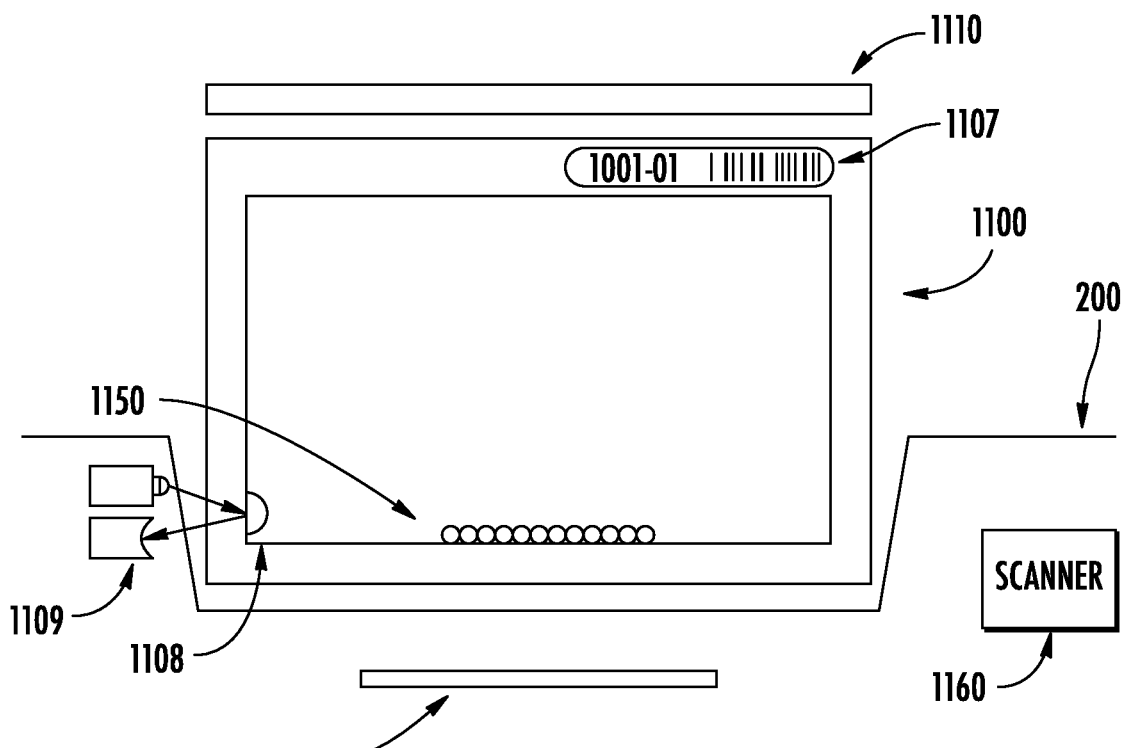
FIG. 18 is an illustration of an example cell culture consumable containing a built in sensor and machine-readable label.

Referring to FIGS. 11-18, an example optical cell culture consumable and system are described. The cell culture consumable can include a container. Optionally, the container includes an integrated optical element (e.g., lens, a microlens, a filter, a prism, a mirror, a light guide, or a textured surface). Alternatively or additionally, the container optionally includes an integrated electrode (e.g., container 100 as described with regard to FIGS. 1-8). The system can include an optical emitter and detector that can be configured in a variety of layouts. Said consumable can optionally include a machine-readable tag (e.g., as shown in FIG. 18) unique to each consumable to automate tracking of culture characteristics and history.

An example optical system can include a single light source or an array of light sources. Example light sources include, but are not limited to, light emitting diodes (LEDs), fluorescent lights, or lasers. As described herein, the light source may be movable, e.g., provided on a movable stage. The light source can be projected over the culture consumable through a mirror, prism, or built-in light guide (e.g., optical elements). In some implementations, the optical element(s) are external to (and separate from) the consumable. In other implementations, the optical element(s) are integrated into the consumable. A single light source can be moved to address each of the consumables in the system, or the system can include an array of light sources. In some implementations, a respective light source is provided for each of a plurality of consumables. Additionally, fiber optics can be used to distribute light from a single source to different areas of the system. The illumination can be optimized to improve sensitivity by relying on phase contrast, dark field, or polarized modalities and it can be Khöler, diffuse, or critical. Narrow bandwidth illumination in either visible, infrared, or ultraviolet ranges can be used to either excite the fluorescence of proteins or dyes or to maximize contrast by relying on the absorption spectra of lipids and proteins or on the refraction angle of the different light wavelengths on the container and cells.

Additionally, the optical cell culture consumable can include an integrated optical light guide or fiber optics (e.g., as shown in FIG. 17) to distribute light throughout the culture vessel either on the side, top or bottom. The light guide can be used to direct or focus light onto the culture to enhance illumination or allow illumination in a manner that can be scaled to multiple culture vessels. It can also be used to direct the light that has been refracted or reflected by the cells in culture to illuminate a detector.

Figure 11:
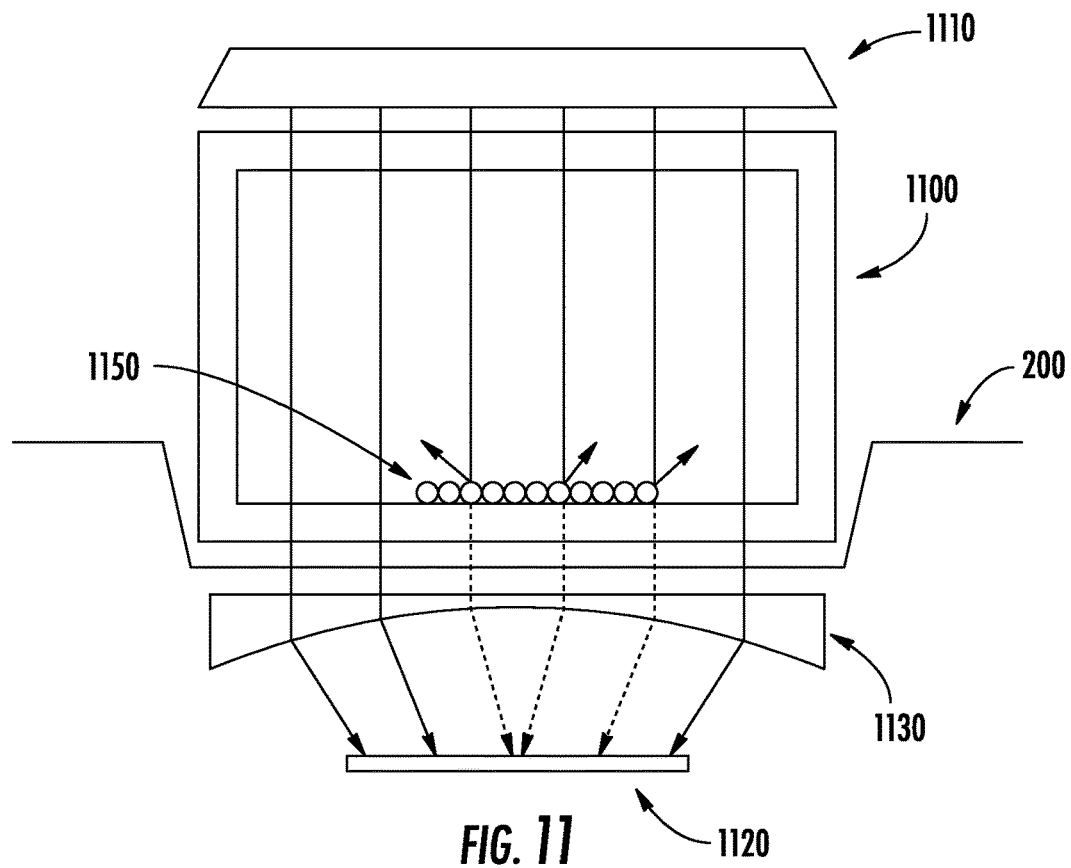
FIG. 11 is another illustration of an example cell culture consumable according to implementations described herein.
Figure 12:
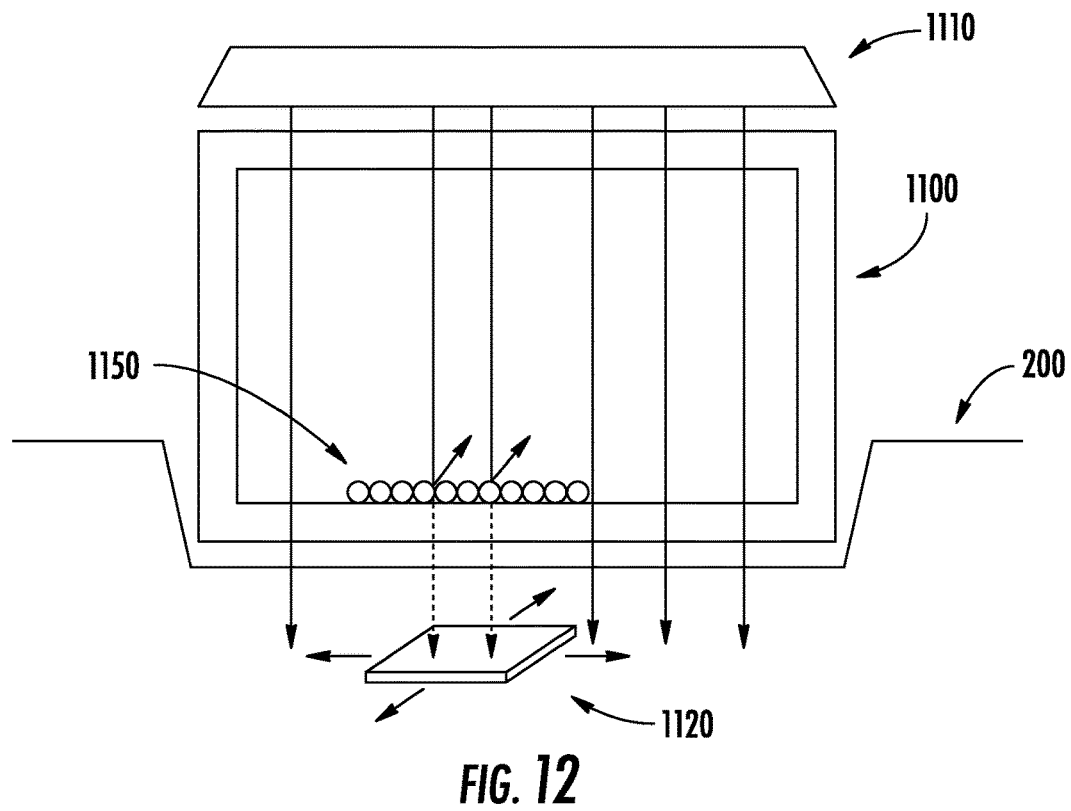
FIG. 12 is another illustration of an example cell culture consumable according to implementations described herein.
Figure 13:
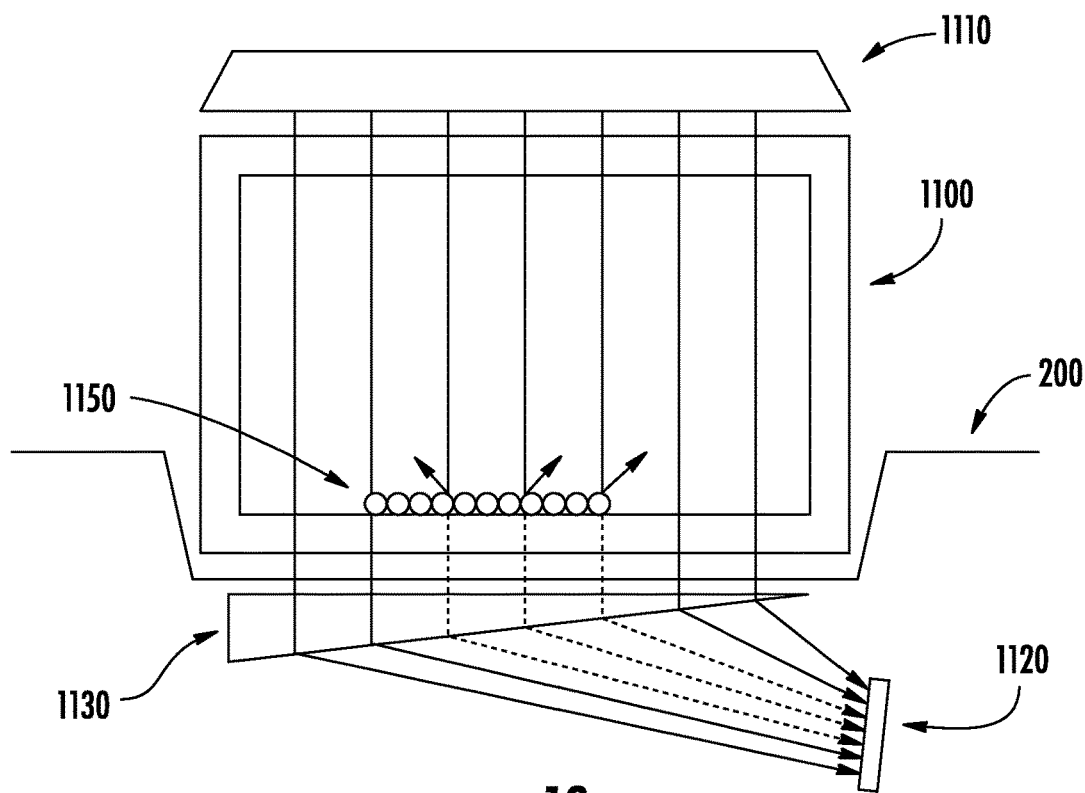
FIG. 13 is another illustration of an example cell culture consumable according to implementations described herein.
Figure 14:
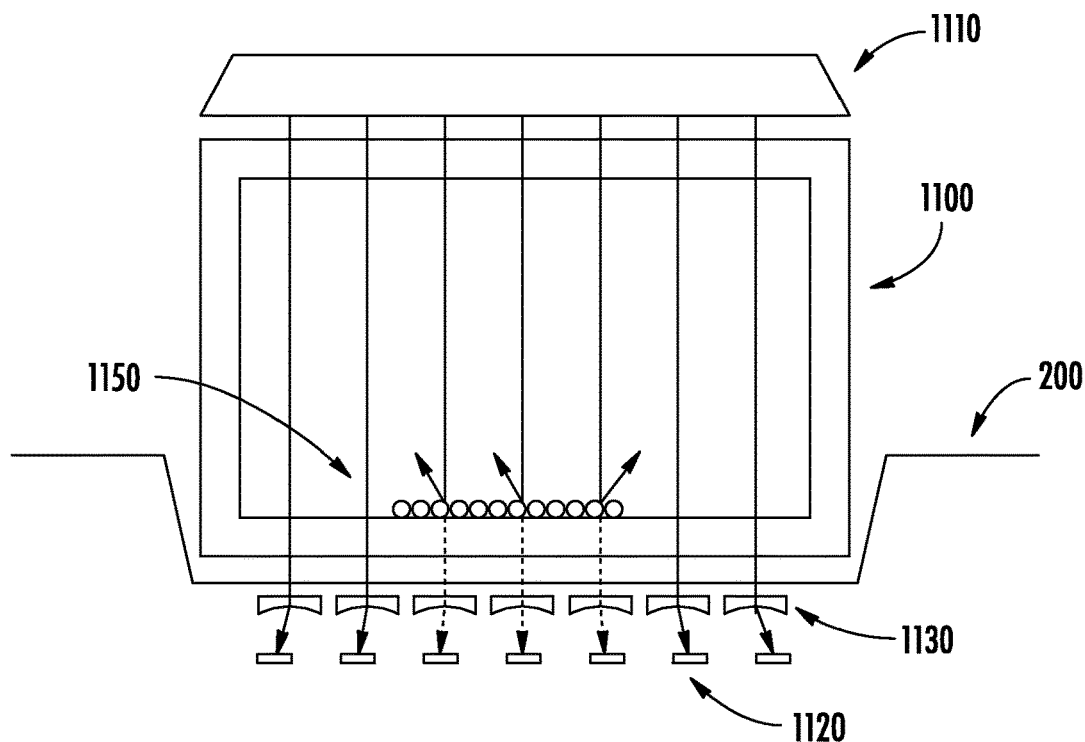
FIG. 14 is another illustration of an example cell culture consumable according to implementations described herein.
Figure 15:
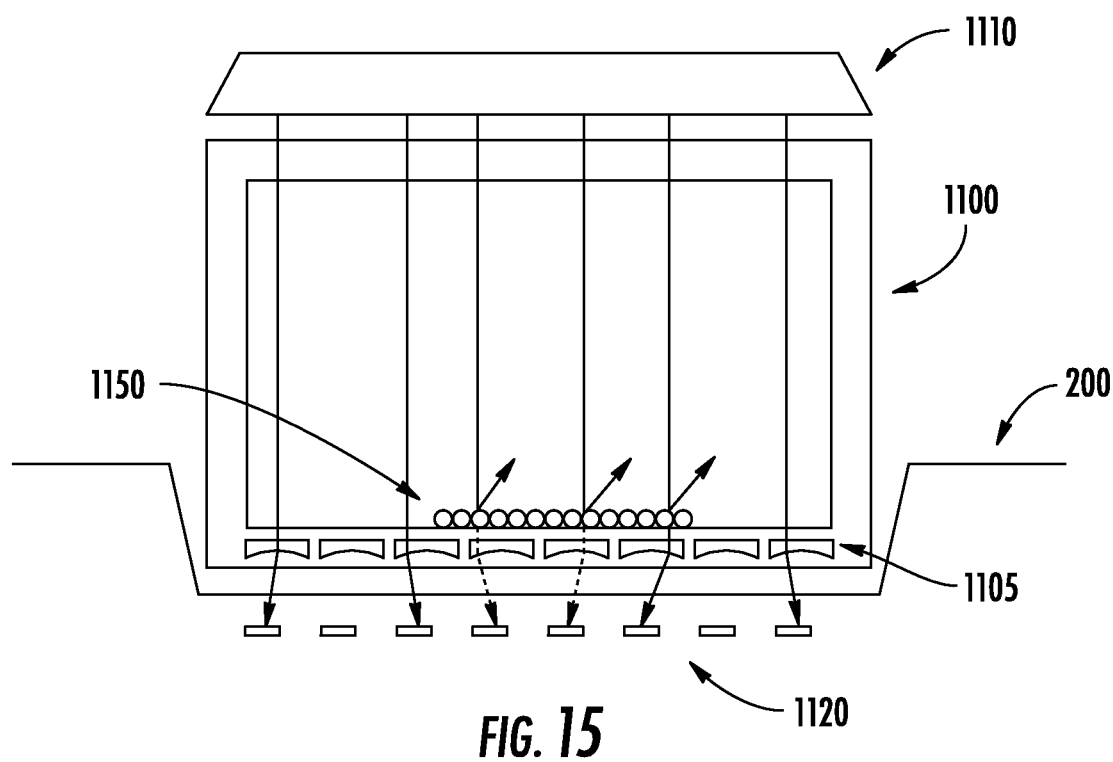
FIG. 15 is another illustration of an example cell culture consumable according to implementations described herein.

Optical systems can include a detector or an array of detectors. Detectors include, but are not limited to, a photo detector, sensor, charge-coupled device (CCD), or camera. In some implementations, the system includes a single optical detector (e.g., as shown in FIG. 12) that is moved to address each culture vessel. In other implementations, the system includes an array of detectors (e.g., as shown in FIGS. 14 and 15) distributed throughout the system. As described herein, the detector may be movable, e.g., provided on a movable stage. For example, the optical system can include a moveable detector or array of detectors that can move in one, two, or three axes. Said detector can be located at the end of a light guide to receive light that has been refracted or reflected by the cell culture, or can be located above or below the culture for a light or bright field image. Imaging of sections of the culture vessel can be obtained via optical fiber-bundles that allow the distribution of sensing areas, while centralizing the required light source and detector elements. Simplified sensing can be obtained via the light escaping from the culture growing directly on a light guide (e.g., as shown in FIG. 13). For all implementations of the optical system, features can be used to obtain 2D information. For example, light guides (e.g., as shown in FIG. 17) built into the flask can be divided into imaging lanes with multiple emitters and detectors or a single set of emitter and detector scanning through the lanes. The light detector can have an integrated lens or mirror (e.g., as shown in FIGS. 11 and 13). Texturing on the surface (e.g., as shown in FIG. 16) used to grow cells can be used to generate more optical contrast as the cells grow and fill in textured areas.

Additionally, lenses or microlenses (e.g., as shown in FIG. 15) can be built directly into the consumable culture vessel. In other words, the lenses or microlenses can be integrated into the container. Lenses integrated into the culture vessel can be optionally created by directly molding the lenses into the vessel glass or plastic during initial vessel formation. To reduce the size and space of optical elements, or to improve detection sensitivity by allowing for 3D information to be gathered, computational optics or light field imaging can be used.

The optical system can be used for optical stimulation, optical measurement, or both. Thus, the optical system can be used for fluorescence, luminescent, chemoluminescent, assays or other measurements of absorption or transmission that can reveal information including cell density. Optical stimulation can also be used to influence cells via well-known photobiological or optogenetic processes. In addition to optical systems to monitor cell culture confluence over time, optical sensors can be used to track cell culture media conditions such as pH, $O_2$ concentration, $CO_2$ concentration, biomass, etc. For example, fluorophore sensors (e.g., as shown in FIG. 18) can be integrated into the vessel walls, positioned directly above the adherent cell culture but still submerged in the media. In another embodiment, sensors can be integrated into the same surface as the cells and illuminated and imaged using optical techniques.

The optical system (e.g., light source(s) and detector(s)) can be used to image the cell culture consumables. Each measurement can image the entire bottom of the consumable, or image a smaller subset of the culture within the consumable. Multiple smaller images can be combined to establish an overall measure of culture confluence and uniformity across the entire consumable. Each sensor can optionally include a filter or lens to enhance optical detection. Filters can be used to measure very specific wavelengths of light to simplify confluence evaluation or enhance contrast. Lenses can be used to resize or focus the desired image or direct the measured image onto the detector. In addition, mirrors, waveguides or prisms can be used to direct the transmitted, refracted or reflected light onto a sensor. These can be built into the system, or integrated into the consumable. These techniques can be used to enhance imaging or to shrink the device, providing the opportunity to scale up to multiple systems. In addition, prisms, waveguides, texturing, and lenses can be built into the consumable. These modifications can be made during the manufacturing process, either through injection molding or other means. These techniques can be used either in small areas, also providing windows for traditional inspection techniques, or across the entire consumable. Waveguides and prisms can be used to direct light that is reflected, refracted, or transmitted through the cells to a single detector or set of detectors. Waveguides can also be used to set up lanes of detection, in which a light is directed into the lane, and total internal reflection is used to keep the light contained in the channel, unless there are cells present to disrupt the total internal reflection. A detector at the other end of the lane then measures how much light was not refracted. Texturing or interference patterns can be used to detect the presence of cells. Cells growing on the texturing will change the coefficient of reflection of the consumable interface, enhancing confluence detection. Lenses and microlenses can be built into the consumable to aid with magnification and light field imaging techniques.

For the purpose of measuring media characteristics, dissolved organic molecules, and gas concentration or to evaluate specific-purpose chromatophores, transmitted or reflected light spectra can be employed with the use of a light source (wide-band, narrow-band, or laser) and a compact spectroscopic sensor which can be an inexpensive solid state photodiode array or a combination diffraction grating with a camera array. Through the use of absorption, reflection, or Raman scattering spectra it becomes possible to extract molecular fingerprints in the media or to evaluate the color of chromatophores embedded in the culture vessel. In addition to directly working with dissolved substances, the same methodology can be used with culture media in the presence of indicator substances such as the commonly used Phenol Red as a pH indicator.

Figure 3:
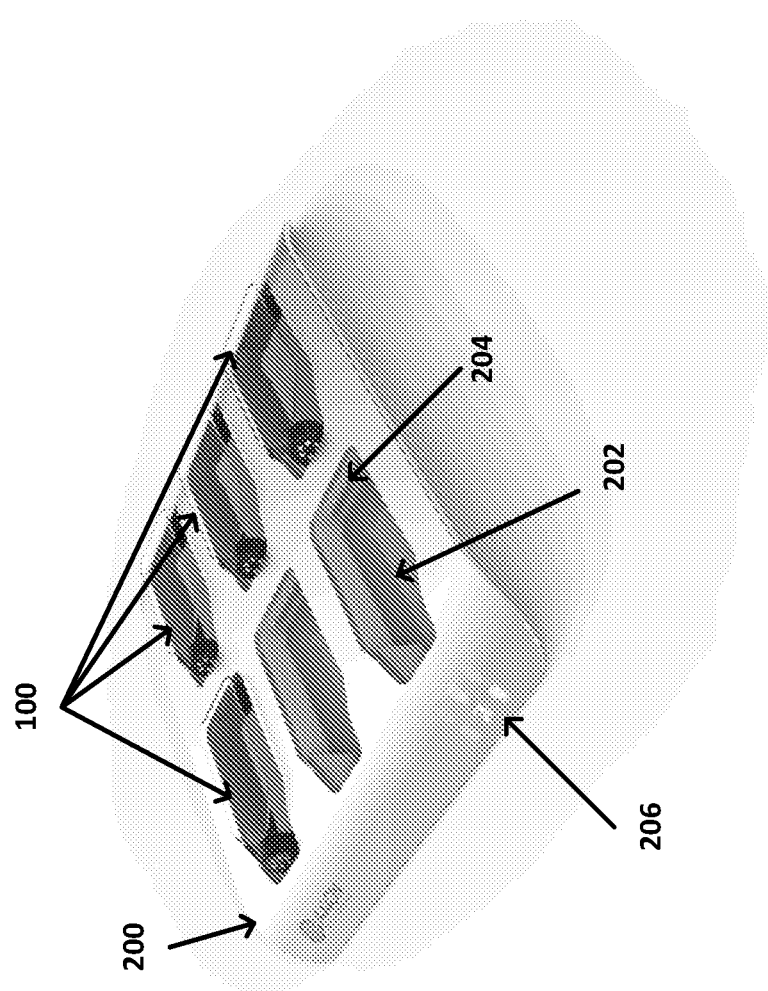
FIG. 3 is an illustration of a tray for receiving cell culture consumables according to implementations described herein.
Figure 4:
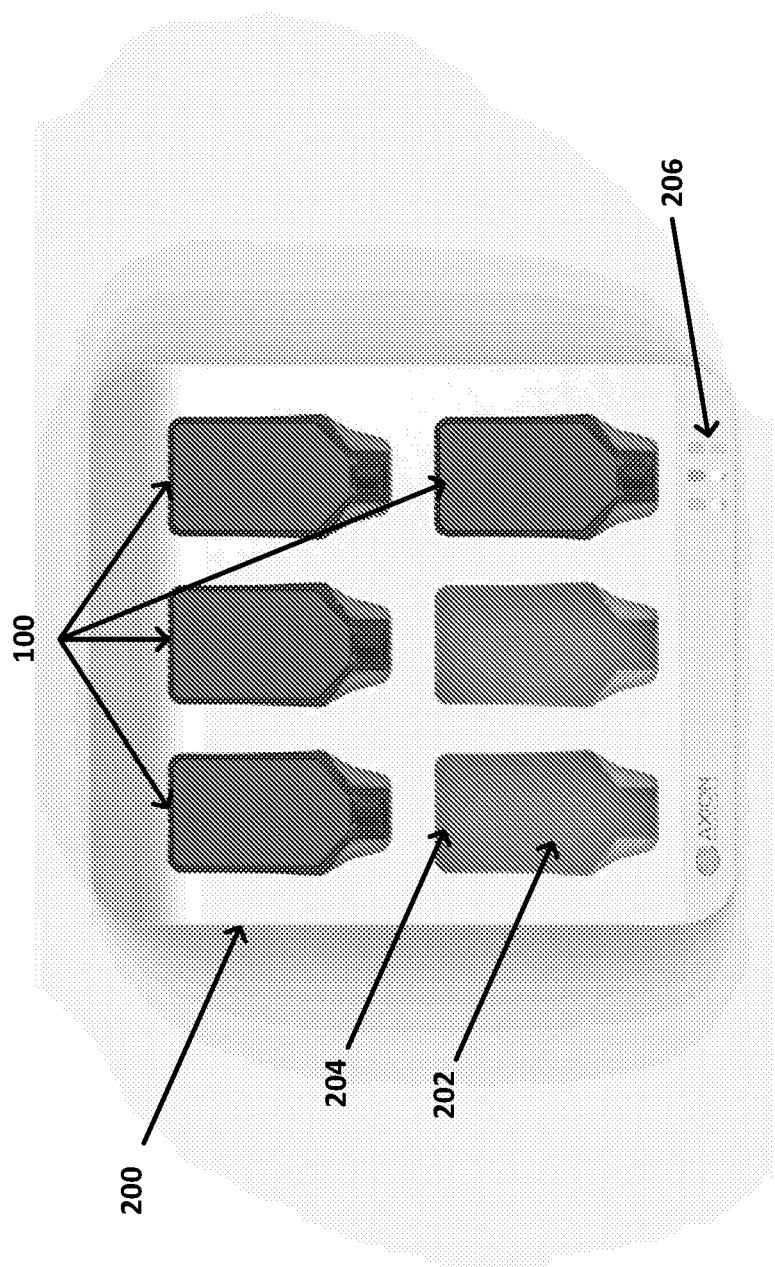
FIG. 4 is another illustration of a tray for receiving cell culture consumables according to implementations described herein.

The example optical system can include a tray or drawer (e.g., tray 200 as shown in FIGS. 3-8) with one or more slots (e.g., slots 202 as shown in FIGS. 3-4) include docking features providing an easy and consistent docking of the culture consumable, such that the consumable is forced into a fixed position. The consumable can include a barcode, which is identified through optical scanning for culture vessel identification. Each slot positions the culture vessel in alignment with the optical imaging system. Optionally, the culture vessel may have fiducial markers integrated into the bottom of the vessel; said fiducial markers serve as reference points, allowing for consistent registration of images despite moving or shifting of the consumable.

Referring now to FIGS. 11-18, an example cell culture consumable and example optical-based system are described. For example, a cell culture consumable can include a container 1100. As described herein, the container 1100 can be a flask, a bottle, a cell culture bag, a Petri dish, or a bioreactor. Optionally, in some implementations, an optical element 1105 is integrated into the container 1100. FIG. 15 illustrates a container 1100 where the integrated optical element 1105 is a plurality of lenses. FIG. 16 illustrates a container 1100 where the integrated optical element 1105 is a textured surface. FIG. 17 illustrates a container 1100 where the integrated optical element 1105 is a light guide. It should be understood that lenses, textured surfaces, and light guides are provided only as examples in FIGS. 15-17. This disclosure contemplates integrating other types of optical elements into the container 1100, which include, but are not limited to, a mirror, waveguide, filter, or prism. The optical element 1105 is built into the container 1100 in FIGS. 15-17. The optical element 1105 can be built into the container 1100 during the manufacturing process, for example, through injection molding or other fabrication process. In this way, the optical element 1105 is part of the container 1100. It should be understood that integrating an optical element into a consumable is different than merely attaching, fixing, etc. the optical element to the consumable (or placing the optical element adjacent to the consumable). This disclosure contemplates that the example cell culture consumable and system can be used to monitor adherent cells 1150. Alternatively or additionally, this disclosure contemplates that the cell culture consumable can be used to monitor cell suspensions.

In some implementations, the cell culture consumable can optionally include a sensor configured for at least one of neurotransmitter sensing, pH sensing, oxygen sensing, glucose sensing, or chemical sensing. Optionally, such a sensor is integrated into the container 1100. As described herein, the sensor can be used to monitor environmental conditions inside the cell culture consumable and/or cell culture medium itself. For example, FIG. 18 illustrates a cell culture consumable including a fluorophore sensor, e.g., sensor 1108 and light emitter/detector 1109.

Alternatively or additionally, the cell culture consumable can include a machine-readable tag 1107 such as a computer readable identifier, label, one-dimensional (1D) or two-dimensional (2D) bar code, or RFID tag.

In some implementations, the container 1100 can define an opening, and the cell culture consumable can include a lid for sealing the opening. The lid maintains a sterile environment within the container.

An example optical system is also described herein. The system can include a plurality of cell culture consumables. Optionally, the cell culture consumable can include an optical element (e.g., as described with regard to FIGS. 15-17) and/or electrode (e.g., as described with regard to FIGS. 1-8) integrated into the container 1100. Alternatively, the cell culture consumable can be a standard consumable (e.g., without integrated optical element and/or electrode). Optionally, the cell culture consumable can include a machine-readable tag 1107 and/or a sensor for detecting environmental or culture medium conditions. The machine-readable tag 1107 can be computer-readable label such as a 1D or 2D bar code. Alternatively, the machine-readable tag 1107 can be an RFID tag. It should be understood that bar codes and RFID tags are provided only as example machine-readable tags. This disclosure contemplates that the machine-readable tag 1107 can be any type of identifier provided on the container 1100 (e.g., printed on, embedded in, disposed on, attached to, etc.) that are capable of being read by a machine.

The system can also include a tray 200 including a plurality of slots configured to receive the cell culture consumables. Trays 200 are described in detail above with regard to FIGS. 1-8. This disclosure contemplates that the trays 200 can be stored in an incubator as described herein. Additionally, the system can include an optical system including a light source 1110 and a detector 1120. This disclosure contemplates that the light source 1110 can be a light-emitting diode (LED), fluorescent light, incandescent light, or a laser. The system can optionally include a plurality of light sources 1110, for example, an array of light sources. Alternatively or additionally, the system can include a light guide (e.g., fiber optic) for distributing light emitted by the light source 1110 throughout the system. Additionally, this disclosure contemplates that the detector 1120 can be a photodetector, camera, charge coupled device (CCD), or other type of light sensor. The system can include a plurality of detectors 1120, for example, an array of detectors (see e.g., FIG. 14). The optical system can be configured to continuously monitor at least one of cell growth, cell proliferation, or cell morphology over time based on an amount of light detected by the detector after reflection, refraction, or transmission by a cell culture 1150. An electronic unit (e.g., electronic unit 300 as described herein) can be used to evaluate cell growth in small sample areas throughout the culture consumable. These samples can be used to establish growth and variability both within each sample and across the entire consumable, to provide measures of overall confluence, and variability or patchiness. Additionally, the electronic unit can compute growth rate, and changes in growth rate of the overall culture can be used to evaluate culture health, and predict when the culture will reach confluence. In some implementations, larger detectors and lower magnifications will be used to establish these measures based on a larger more complete image of the consumable, instead of smaller sample sizes. In some implementations, the optical system can be configured to simultaneously monitor at least one of cell growth, cell proliferation, or cell morphology in each of the cell culture consumables. Optionally, in some implementations, the optical system can be further configured to monitor a cell culture medium (e.g., using sensor shown in FIG. 18). Graphical processing methods can be used to evaluate the color of the culture medium, which often includes Phenol Red to determine culture pH. This may include using a control color to establish and/or calibrate the pH scale. Alternatively, optical processing methods can be used to distinguish between growing adherent cells, cells floating in media and cloudy, contaminated media. These measures can be used to track environmental conditions.

In some implementations, the system includes a system optical element 1130, which is not part of the cell culture consumable. FIG. 13 illustrates a system where the optical element 1130 is a prism. FIG. 14 illustrates a container 1100 where the optical element 1130 is a plurality of lenses. It should be understood that prisms and lenses are provided only as examples in FIGS. 13-14. This disclosure contemplates integrating other types of optical elements into the system such as a mirror, waveguide, filter, etc. This disclosure contemplates that the system can include cell culture consumable with integrated optical elements (e.g., as shown in FIGS. 15-17) or without integrated optical element. This disclosure also contemplates that the system can include cell culture consumables with integrated electrodes (e.g., as described above with regard to FIGS. 1-8).

Optionally, the optical system can further include a scanner 1160 configured to read a machine-readable tag 1107 provided on the containers 1100, e.g., as shown in FIG. 18.

In some implementations, the system can include an incubator (e.g., incubator 400 shown in FIGS. 7 and 8) configured to receive the tray 200. Optionally, the system can include a plurality of trays, where each tray 200 includes a plurality of slots configured to receive the cell culture consumables.

Figure 5:
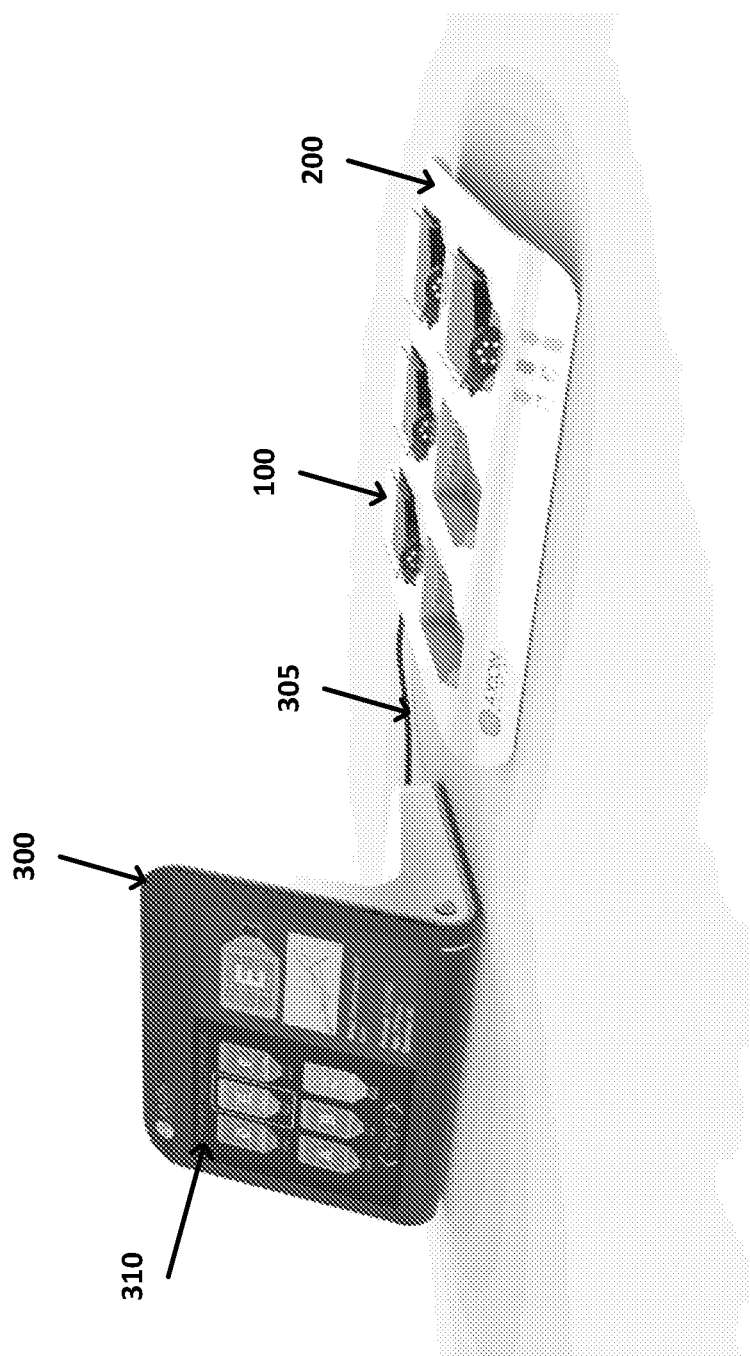
FIG. 5 is an illustration of an electronic unit (e.g., console) operably coupled to a tray for receiving cell culture consumables according to implementations described herein.
Figure 6:
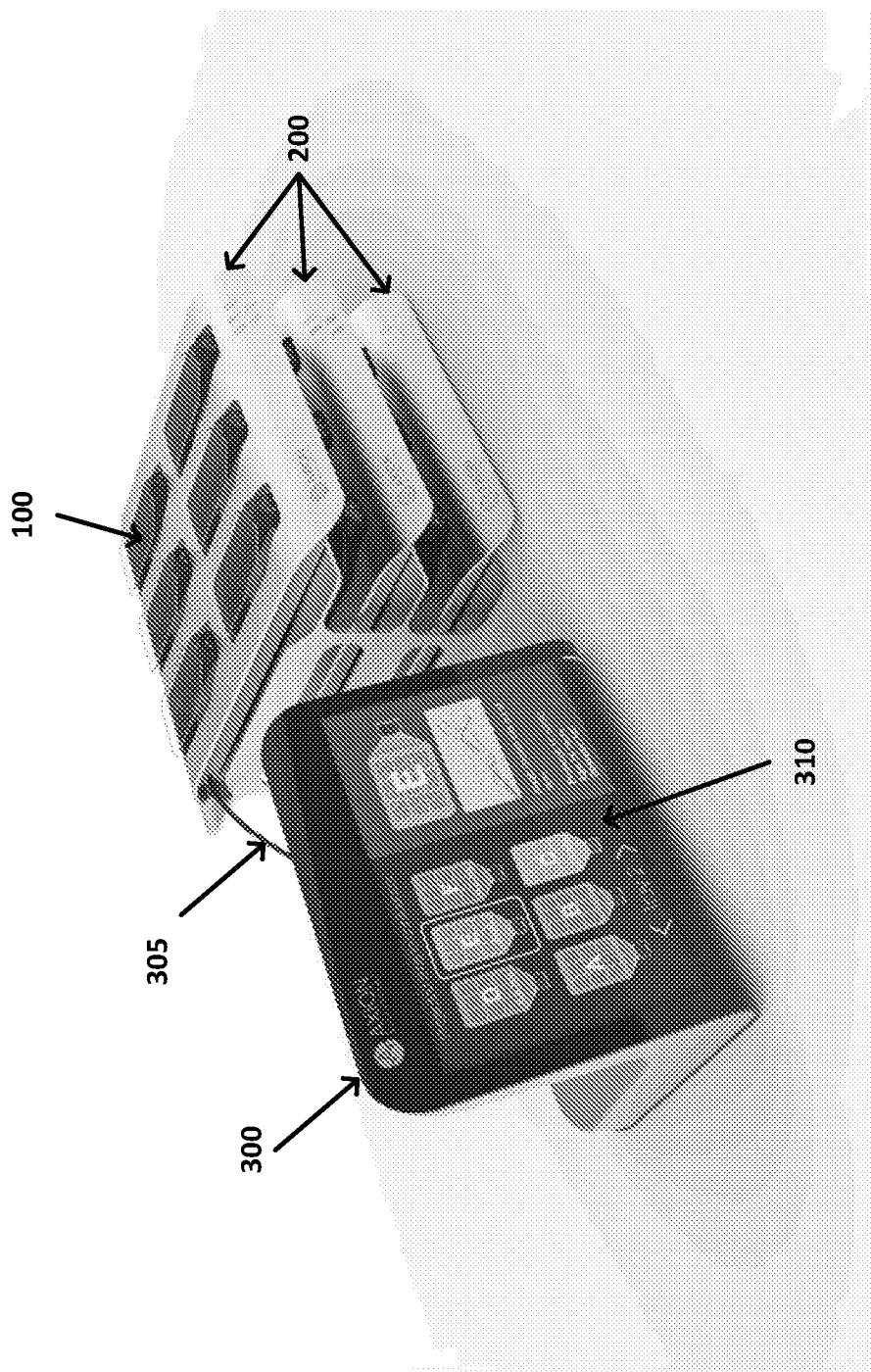
FIG. 6 is another illustration of an electronic unit (e.g., console) operably coupled to a plurality of trays for receiving cell culture consumables according to implementations described herein.
Figure 7:
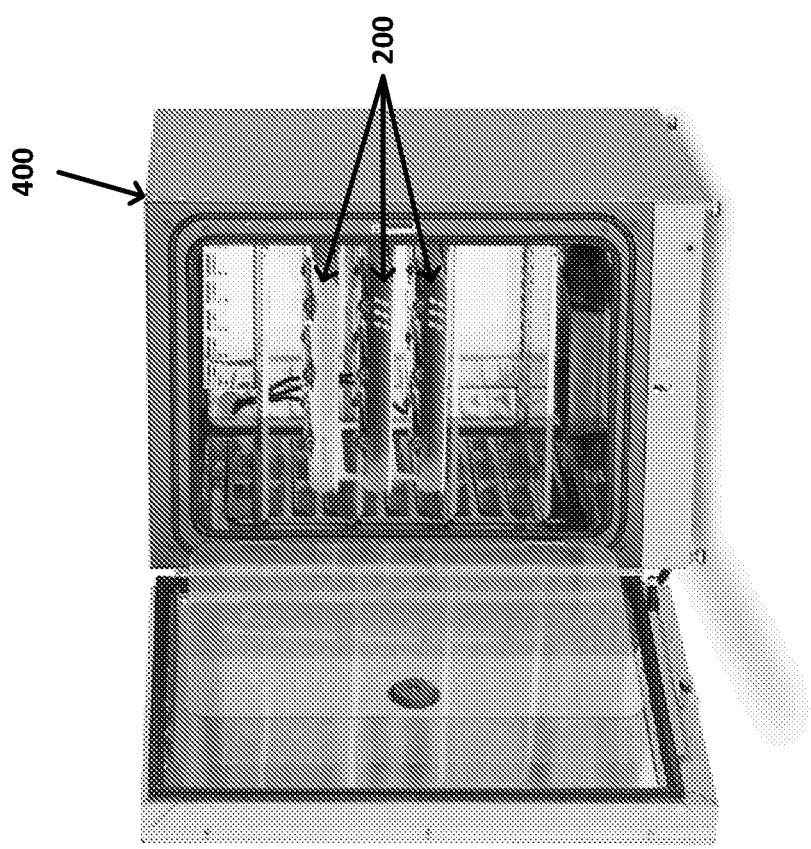
FIG. 7 is an illustration of an incubator for receiving trays according to implementations described herein.
Figure 8:
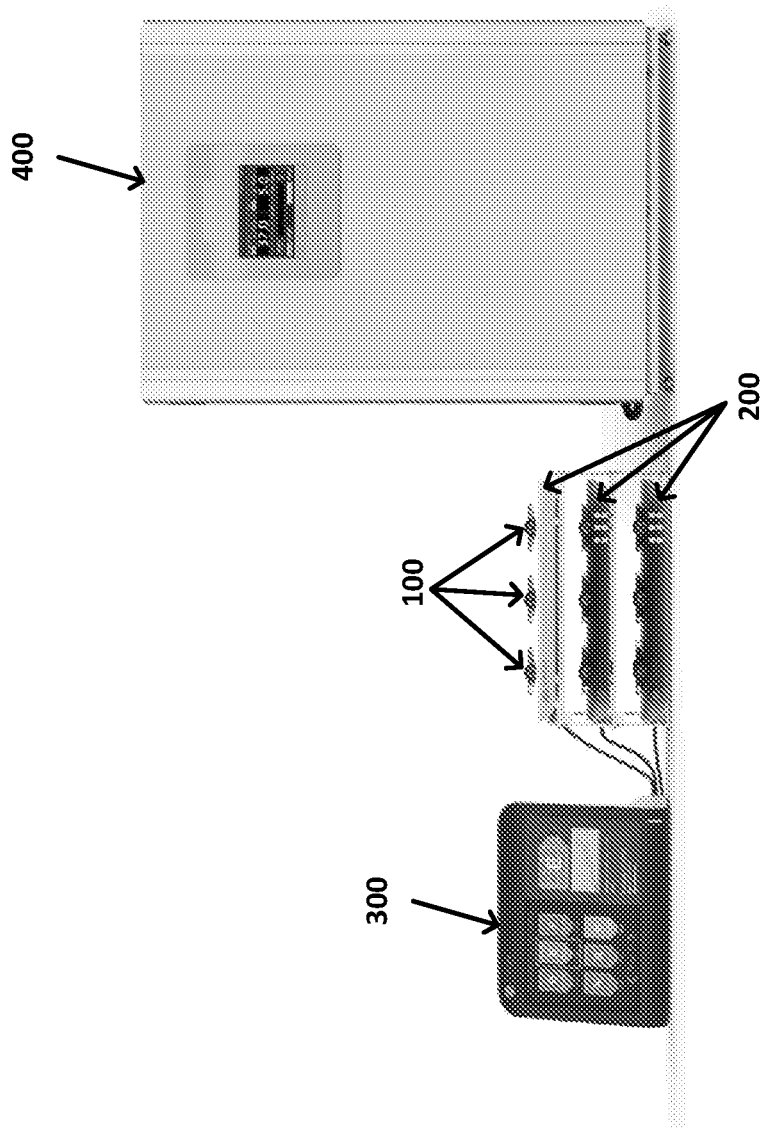
FIG. 8 is an illustration of trays for receiving cell culture consumables, an electronic unit (e.g., console), and an incubator according to implementations described herein.

In some implementations, the system can include an electronic unit (e.g., electronic unit 300 shown in FIGS. 5, 6, and 8). The electronic unit can be operably coupled to the optical system by a communication link, e.g., any link that facilitates data exchange between the electronic unit and the optical system. The electronic unit can be configured to control the light source 1110. The electronic unit can be configured to record signals collected by the optical system (e.g., signals detected by the detector 1120). This information can be stored in memory of the electronic unit. Alternatively or additionally, the electronic unit can be operably coupled to the tray 200 through a communication link (e.g., communication link 305 shown in FIGS. 5 and 6). Optionally, in some implementations, the electronic unit can be incorporated into the tray 200. The electronic unit can be configured to record the amount of light detected by the detector after reflection, refraction, or transmission by the cell culture 1150. Alternatively or additionally, the electronic unit can be configured to record characteristics of light (e.g., frequency) detected by the detector after reflection, refraction, or transmission by the cell culture 1150.

The electronic unit can be configured to measure cell confluency of the cell culture. Graphical processing methods can be used to identify cell bodies and count the number of cells in the imaging area. Alternatively, the electronic unit can optionally then establish sizes for identified cell bodies. Quantification of number of cells and/or average size of each cell can be used as a measure of cell growth and/or growth rate. Additionally, the amount of the imaged area covered by cells can be calculated. Changes in this coverage area can be used as a measure of growth rate. For example, the electronic unit can be configured to generate a two-dimensional map of the cell confluence across the at least one of the cell culture consumables. Optionally, the electronic unit can be configured to create a real-time growth curve using the cell confluence for the at least one of the cell culture consumables. Optionally, the electronic unit can be configured to analyze the real-time growth curve and provide in-process control feedback for the at least one of the cell culture consumables. In-process control feedback can be provided in response to the signals collected by the optical system (e.g., the amount and/or characteristics of light detected by the detector 1120) and optionally analyzed by the electronic unit. The in-process control feedback can be a visual display (e.g., display device 310 as shown in FIGS. 5 and 6), an audible alarm, an email, a text message, or combinations thereof.

This disclosure contemplates using 3D imaging such as light-field imaging techniques or digital inline holographic microscopy (DIHM) techniques to measure cell confluence, cell-cell junction strength, or adhesion strength of the cell culture. In other words, the electronic unit described herein can be configured to analyze the signals collected by the optical system using light-field imaging or DIHM imaging. Light-field imaging and DIHM imaging are computational optics techniques that are known in the art. These techniques reduce and/or remove the need to provide a complex lens system. It should be understood that this reduces the size and space required for the optical system described herein.

Light-field imaging techniques include acquiring information regarding the incident light-field into a sensor (intensity, color, and direction) instead of merely a 2D image on the focus plane. This light-field allows for the computation of different 2D images from different image planes of the same optical data or the reconstruction of a 3D scene from the captured information. The DIHM imaging technique includes generation of one or more coherent light fields, using lasers or other monochromatic sources via individual pinholes (and possibly narrow-band filters in the sensing elements), and detecting the resultant interference patterns with a high-resolution light sensing array (such as a complementary metal oxide semiconductor (CMOS) or CCD imager). The resulting captured interference hologram provides the necessary information from the light front for the reconstruction of light intensity 2D images or, by capturing two or more images from different wavefronts or spacings, 3D scenes and phase images. Both techniques make use of modeling the light wave-fronts based on the specific system geometry but, given mechanical imperfections that could be considerably larger than the illumination wavelength. Additionally, machine learning techniques can be used to reliably produce better images (particularly for DIHM). Although the amount of computation required to obtain an image via these computational methodologies can be relatively high, particularly when dealing with multiple separate image elements in multiple culture vessels, the relatively slow sampling requirements on the order of less than once a minute to a few times an hour provide enough time for detailed image processing.

Optionally, the system can further include a sensor configured for at least one of neurotransmitter sensing, pH sensing, oxygen sensing, glucose sensing, or chemical sensing. Optionally, the sensor can be integrated into the cell culture consumable. For example, FIG. 18 illustrates a cell culture consumable including a fluorophore sensor, e.g., sensor 1108 and light emitter/detector 1109. The electronic unit can be configured to receive a signal from the sensor. Optionally, the electronic unit can be configured to provide in-process control feedback based on the signal received from the sensor. The in-process control feedback can be a visual display (e.g., display device 310 as shown in FIGS. 5 and 6), an audible alarm, an email, a text message, or combinations thereof.

Figure 19A:
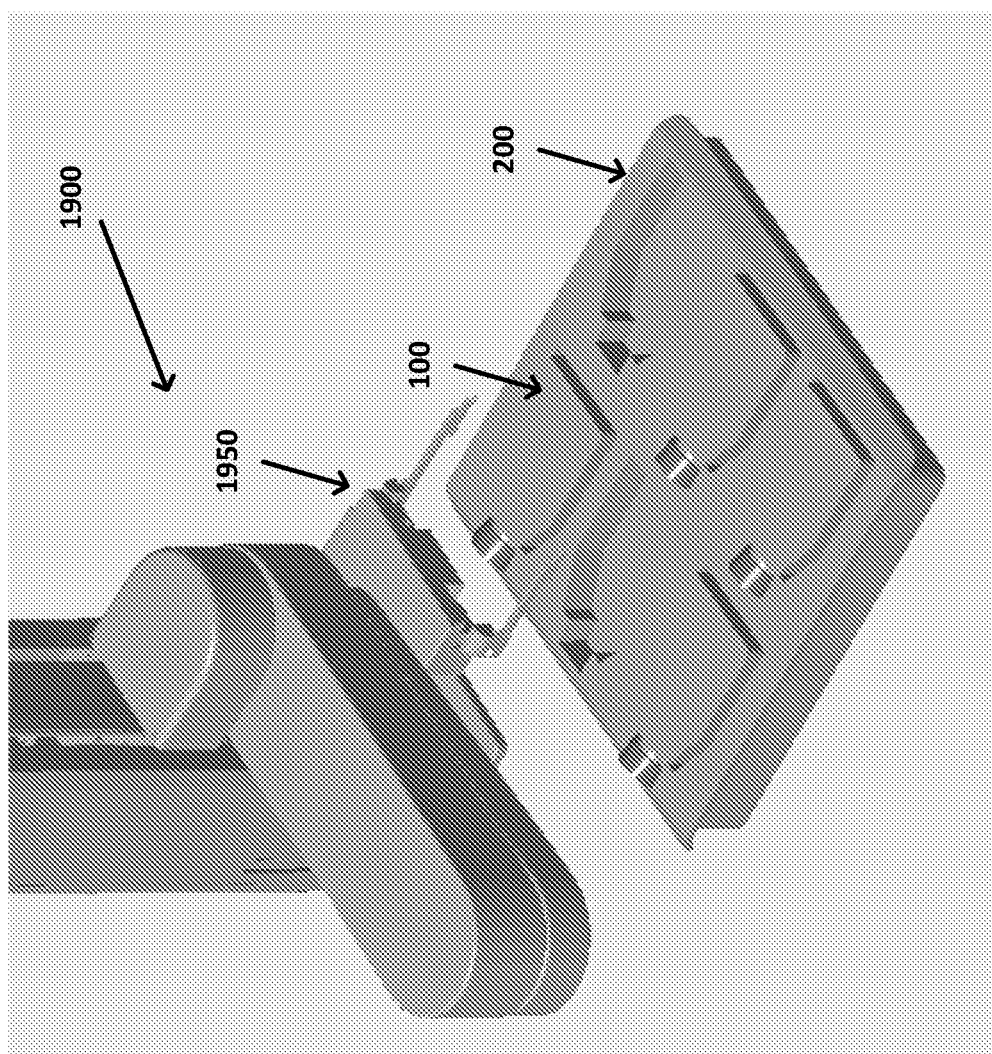
FIGS. 19A-19B illustrate an example system including a robot according to implementations described herein.
Figure 19B:
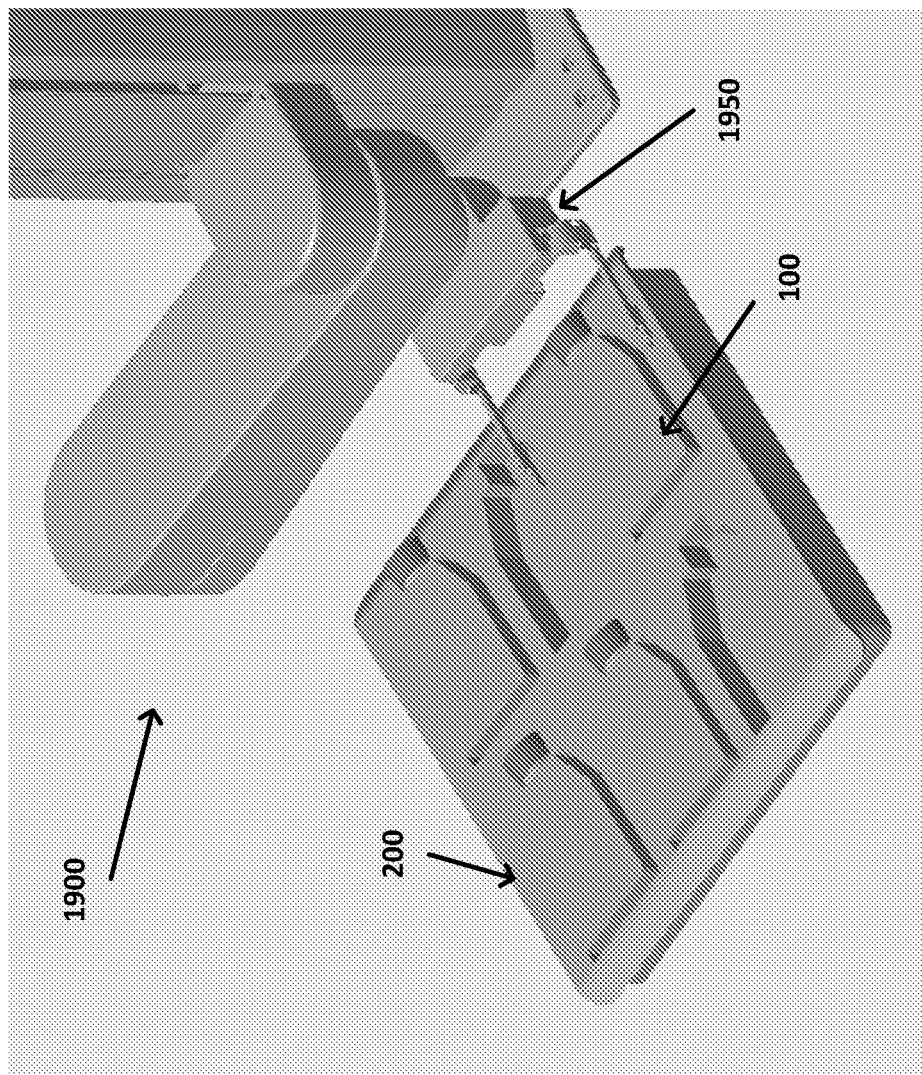

Optionally, in some implementations, the system can include a robot having a robotic arm, for example, as shown in FIGS. 19A and 19B. Optionally, the robot is operably coupled to the electronic unit. The electronic unit can be further configured to control the robotic arm to pick up and move the tray or the cell culture consumable from a first position to a second position. For example, the robot can be used to transfer a tray to/from the incubator. Alternatively or additionally, the robot can be used to transfer a cell culture consumable to/from the tray.

Another example method is also described herein. The method can using include a standard container or one with built-in optics to facilitate confluence imaging, whereby light is used to illuminate the culture and basic measures of reflected or refracted light or other imaging techniques are used to quantify cell culture confluence.

Another example method is also described herein. The method can include illuminating a cell culture in at least one of a plurality of cell culture consumables; detecting an amount of light reflected, refracted, or transmitted by the cell culture; and continuously monitoring at least one of cell growth, cell proliferation, or cell morphology of the cell culture over time.

In some implementations, the method can further include measuring cell confluency of the cell culture. In some implementations, the method can further include measuring pH, oxygen concentration, glucose concentration, or chemical concentration within the at least one of the cell culture consumables. In some implementations, the method can further include optically monitoring a cell culture medium. In some implementations, the method can further include providing in-process control feedback for the at least one of the cell culture consumables. Additionally, this disclosure contemplates that one or more signals can be recorded from each of a plurality of cell culture consumables. Optionally, such signals can be collected from a plurality of cell culture consumables simultaneously.

The devices and systems described herein use a combination of mechanical and electrical design, along with electrode designs and/or optical systems and fabrication methods, to achieve a simple-to-use, non-invasive, scalable cell monitoring system capable of monitoring dozens to hundreds of cell culture consumables simultaneously. This disclosure contemplates using the cell culture consumables, systems, and methods described herein for the following applications.

The devices, systems, and methods described herein can be used to estimate the time of "splitting" or "passaging" of cells. Splitting cells is the process by which the rate of cell proliferation is maximized by separating them (splitting) into different culture flasks before a certain cell density is reached. For example, when bulking-up (i.e. increasing the cell number) the human induced pluripotent stem cells (hiPSC) starting material, the operator has to use judgement as to when the cell culture has reached the optimal confluency/density. Cell culture confluency describes the percentage of cell culture area covered by adherent cells. This measure is important for determining the optimal timing for splitting cells. Allowing cell culture batches to reach high cell confluency is typically not desirable. For example, contact inhibition can cause reduction in cell size or plate detachment. Splitting at 70-80% confluency takes cells that are still growing exponentially (near the end of the log phase) and will result in improved overall cell viability, yielding cells that are less aggregated and reducing the lag time (idle time before the cells start logarithmic growth once again.) Precise visual determination by the operator of cell confluency is difficult, even for an expert trained and experienced scientist.

Using the devices, systems, and methods described herein, however, electrical impedance or optical confluence measurements can give a real-time growth curve from each flask notifying the operator of the optimal time to split their cells. Similar real-time feedback can also signal to the operator to discard slow or abnormally-growing cell flasks. This disclosure contemplates that the cell culture consumables and/or system described above with regard to FIGS. 1-18 can be used to collect such impedance and confluence measurements. Such a system can reduce requirement for an expert to make intuitive "gut feeling" decisions regarding process control.

Additionally, during cell manufacture, it is typically desirable to maintain cells in an exponential growth ("log") phase. When the adherent cells have little space left to grow, they stop dividing, due to growth inhibition. Visual inspection is used to determine confluency (i.e. the space left to grow) of the cell culture. It is understandable that proliferating cells will, for example, respond differently to toxic compounds than growth-arrested cells. Conventionally, the operator uses his or her judgment of when to harvest the flask of cells, so that a fraction of the cells can be re-seeded into a new flask to continue the cell culture. The operator needs to inspect each flask on a daily basis to determine the growth status of the flask. The devices, systems, and methods described herein address this problem. For example, an impedance sensor incorporated in the flask (e.g., electrodes 102 incorporated into container 100 in FIGS. 1-8) or automated optical sensing (e.g., using consumables described with regard to FIGS. 11-18) can give a real-time readout of the confluency of the cell culture in the flask, reducing the time spent manually inspecting flasks. Optical techniques described herein, could additionally capture periodic snapshots of cell growth, providing a record for technicians and advanced quality control capabilities.

Additionally, the devices, systems, and methods described herein allow for flasks (cell culture consumables) to be tracked and managed individually or as linked batches. As discussed above, cell manufacture operates at different scales, with potentially different requirements for the definition of a "batch" of cells, which might include multiple flasks or a single flask depending on the production scale. Flasks tracked individually can provide notifications only on the progress and required steps for that flask. By comparison, management of a batch comprised of multiple flasks using the devices, systems, and methods described herein can algorithmically track each flask and provide an integrated assessment and notification of when to split the flask. In this way, the devices, systems, and methods described herein can reduce labor time and improve efficiency by providing an optimal recommendation across the entire batch, rather than each individual flask. For each flask within a batch, the devices, systems, and methods described herein can utilize information including, but not limited to, the confluency, rate of change of the confluency, and variance across flasks.

The devices, systems, and methods described herein can be used to monitor cell growth curves. Restating earlier concepts, the impedance measured at the electrode is proportional to the number of cells growing over the electrode. Likewise, the amount of light reaching a photodetector after being refracted or reflected by growing cells is also related to the density of cells. So, as the number of cells in the flask increase, the recorded impedance and/or the optical confluence measure also increase. One way to estimate that the cells need to be passaged (split) is to alert the user when the impedance or optical confluence signal starts to flatten off (e.g. the rate of increase drops). However, this technique would be suboptimal as most users would want to prevent the cells from reaching this dense culture phase (because the cells will start to be impacted by contact inhibition which reduces, amongst other things, their growth rate). An alternative technique is for the user to run one (or several flasks) to establish the growth curve profile for their particular cell type of interest. The system can store this information and use this as the standard. A real time result can be compared to this standard to estimate how confluent the flask is (e.g. 50% confluent). The user can set the optimal confluence level, so that they are alerted e.g. when their flasks are 70% confluent. It should be understood that 70% confluence is provided only as an example optimal confluence level. This disclosure contemplates that the optimal confluence level can be more or less than 70%. For example, the optimal confluence level may be between about 50% and about 80%, depending on the cell type.

Similarly, if the flask's growth curve is out of spec relative to the established growth curve of the cells, the devices, systems, and methods described herein can alert the user of the potential problem (e.g., recommend to the user discarding these cells as they are growing too slowly, or maybe these cells are contaminated). In "batch mode" of multiple culture vessels, the average and variance across the growth curves can be compared to the established (e.g. trained) growth curve. In this way, individual flasks can be automatically labeled as outliers and excluded, to improve efficiency of the overall batch growth.

The devices, systems, and methods described herein can be used to estimate the time of cell maintenance/media exchange/growth factor addition. This disclosure contemplates that the devices, systems, and methods described above with regard to FIGS. 1-18 can be used to provide real-time information regarding optimal timing for the addition of growth factors to developing cell batches. Traditional cell manufacturing processes are rigid and expensive growth factor reagents (e.g. small molecules) are added on the day prescribed in the protocol. Using the devices, systems, and methods described herein, impedance or optical confluence measurements can give an insight into the growth/development of the cell culture. Predictive markers can be identified that indicate when to add the next phase of reagents.

Cells grown in culture are routinely "fed" (i.e. their cell culture medium is refreshed) on a pre-determined basis (typically every 2-3 days). The cell culture medium typically contains a color-change indicator that turns from a pink to an orange color as the medium becomes acidified (which indicates that it is time to change the cell culture medium). This is a very crude method but is nonetheless the most commonly used approach for determining when to change the cell culture medium. The devices, systems, and methods described herein can include a pH sensor or $O_2$ sensor, which when incorporated into the culture flask (cell culture consumable), allows the system to notify the operator of the optimal time to replace the media.

In some implementations, it is possible that the type of action recommended by the system (e.g. change/refresh the cell culture medium) can be inferred from more than one type of measurement from the electrodes. For example, based on both the projection of the speed of cell growth (from the impedance electrodes) and also the current pH of the medium, the system can recommend that the medium be refreshed the next day.

In "batch mode", the sensor recordings from each flask of a batch can be algorithmically integrated to provide a single notification or recommendation based on pre-determined or learned optimization scheme to minimize technician contact time and/or maintain consistency across the batch.

This disclosure contemplates that multiple measures of the same or different modalities/measurement types can be used together in decision making processes. For example, the rate of growth or other measure, in combination with additional measures (electrical, chemical, optical, etc.) like impedance, pH, light transmission, fluorescence, etc. can be used together to schedule actions, such when to change/refresh the cell culture medium.

The devices, systems, and methods described herein can be used to estimate the time of cell harvest. This disclosure contemplates that the devices, systems, and methods described above with regard to FIGS. 1-18 can be used to provide real-time information regarding optimal timing for harvesting of the manufactured cell product. Traditional manufacturing processes are rigid, (e.g. cells are harvested on Day 20 of the manufacturing process.) In real-world settings, however, a given batch may require more time or less time to mature before harvesting. Using the devices, systems, and methods described herein, impedance and confluence measurements, for example, can be used to indicate the optimal time to harvest the cell batch. For instance, in the case of hiPSC-cardiomyocytes, impedance and field potential measurements can indicate when the cell batch has reached a stable beat rate. Or, in the case of hiPSC-neurons, field potential measurements can be used to indicate the optimal time to harvest a neural cell batch, as determined by a synchronous network activity phenotype.

In each of the examples above, the functional activity from the cardiomyocytes or neurons can be evoked via integrated methods for electrical or optical stimulation. In this way, the system can enter a "cell harvest" mode, based on pre-set timings from the user, whereby the cells in each flask are periodically probed with stimulation and the functional response monitored.

The devices, systems, and methods described herein can be used to estimate the time for abandoning a cell batch. This disclosure contemplates that the cell culture consumables and/or system described above with regard to FIGS. 1-18 can be used to provide real-time information regarding optimal timing for abandoning a failed batch of cells. Often it is not until the end of a 20+ day manufacturing process that an operator knows whether a cell batch has failed. Abandoning a failing batch (or flask) as soon as possible (i.e. "failing fast, fail cheap") can reduce manufacturing costs. Using the devices, systems, and methods described herein, impedance or optical measurements can allow the operator to discard slow growing cell flasks, or flasks with poor spontaneous beating activity (in the case of hiPSC-cardiomyocytes).

The devices, systems, and methods described herein can be used to establish quality control acceptance criteria around cell preparations used as assays. This disclosure contemplates that the devices, systems, and methods described above with regard to FIGS. 1-18 can be used to provide quality control. The quality of the cells used in the assay will impact the reliability of the test result. The performance of a particular cell preparation in an assay can be compared to the cell culture characteristics prior to harvesting for the assay (growth rate, "patchiness" of the cell culture). This will enable acceptance criteria to be set for cell cultures used in assays thereby improving the reliability of the assay.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A system, comprising:
   a plurality of cell culture consumables, wherein each of the cell culture consumables comprises a container having an internal surface that defines a distinct cell culture environment and a plurality of electrodes, the electrodes being integrated into the container, wherein the electrodes are distributed across an internal surface of the container;
   one or more trays configured for organizing the cell culture consumables; and
   an electronic unit comprising a processor and a memory, the memory having computer-readable instructions stored thereon that, when executed by the processor, cause the electronic unit to:
   record a respective signal collected by the electrodes of each of the cell culture consumables,
   measure impedance for at least one of the cell culture consumables,
   create a real-time growth curve using the impedance for the at least one of the cell culture consumables, and
   estimate cell culture confluency using the real-time growth curve for the at least one of the cell culture consumables.

2. The system of claim 1, wherein the one or more trays comprise a plurality of slots configured to receive the cell culture consumables, and wherein the plurality of slots include at least two slots having different sizes and/or shapes.

3. The system of claim 1, wherein:
   each of the one or more trays comprises a plurality of slots configured to receive the cell culture consumables,
   each of the cell culture consumables and each of the plurality of slots comprises a respective electrical connector, and
   the respective electrical connectors for a corresponding cell culture consumable and slot are configured to be removably coupled to each other.

4. The system of claim 1, wherein the electrodes of each of the cell culture consumables are configured for at least one of impedance sensing, voltage sensing, pH sensing, oxygen sensing, glucose sensing, or chemical sensing, and the memory has further computer-readable instructions stored thereon that, when executed by the processor, cause the electronic unit to measure at least one of impedance, voltage, pH, oxygen concentration, glucose concentration, or chemical concentration for each of the cell culture consumables.

5. The system of claim 4, wherein the memory has further computer-readable instructions stored thereon that, when executed by the processor, cause the electronic unit to monitor at least one of cell growth, cell proliferation, cell morphology, or a cell culture medium for each of the cell culture consumables.

6. The system of claim 4, wherein the memory has further computer-readable instructions stored thereon that, when executed by the processor, cause the electronic unit to provide in-process control feedback for each of the cell culture consumables.

7. The system of claim 1, wherein the memory has further computer-readable instructions stored thereon that, when executed by the processor, cause the electronic unit to measure at least one of pH or oxygen concentration for at least one of the cell culture consumables.

8. The system of claim 7, wherein the memory has further computer-readable instructions stored thereon that, when executed by the processor, cause the electronic unit to analyze the pH or oxygen concentration and provide in-process control feedback for the at least one of the cell culture consumables.

9. The system of claim 1, wherein the memory has further computer-readable instructions stored thereon that, when executed by the processor, cause the electronic unit to deliver electrical stimulation via the electrodes of at least one of the cell culture consumables.

10. The system of claim 1, further comprising an optical module including at least one of a light source or an optical detector.

11. The system of claim 1, wherein the electrodes of each of the cell culture consumables are embedded in the internal surface of the container, or the electrodes of each of the cell culture consumables are disposed on the internal surface of the container.

12. The system of claim 1, further comprising:
an electrical connector arranged on an external surface of the container; and
a plurality of routing traces electrically connecting the electrodes and the electrical connector.

13. The system of claim 1, wherein the container defines an opening, and the cell culture consumables further comprise a lid for sealing the opening, the lid maintaining a sterile environment within the container.

14. The system of claim 1, wherein the electrodes of each of the cell culture consumables are configured for at least one of impedance sensing, voltage sensing, neurotransmitter sensing, pH sensing, oxygen sensing, glucose sensing, or chemical sensing.

15. The system of claim 14, wherein the electrodes of each of the cell culture consumables include a first set of electrodes configured for impedance sensing or voltage sensing and a second set of electrodes configured for at least one of neurotransmitter sensing, pH sensing, oxygen sensing, glucose sensing, or chemical sensing.

16. The system of claim 1, wherein the container is a flask, a bottle, a cell culture bag, a Petri dish, or a bioreactor.

* * * * *